US012216820B2

(12) United States Patent
Yee et al.

(10) Patent No.: US 12,216,820 B2
(45) Date of Patent: Feb. 4, 2025

(54) HEAD MOUNTED DISPLAY WITH VISUAL CONDITION COMPENSATION

(71) Applicant: Penumbra, Inc., Alameda, CA (US)

(72) Inventors: William Ka-Pui Yee, Alameda, CA (US); Jeffrey Peter Bellinghausen, Carlsbad, CA (US)

(73) Assignee: Penumbra, Inc., Alameda, CA (US)

( * ) Notice: Subject to any disclaimer, the term of this patent is extended or adjusted under 35 U.S.C. 154(b) by 0 days.

(21) Appl. No.: 18/673,291

(22) Filed: May 23, 2024

(65) Prior Publication Data

US 2024/0310909 A1 Sep. 19, 2024

Related U.S. Application Data

(63) Continuation of application No. 18/185,254, filed on Mar. 16, 2023, now Pat. No. 12,001,605.

(60) Provisional application No. 63/397,500, filed on Aug. 12, 2022.

(51) Int. Cl.
G06F 3/01 (2006.01)
A61B 3/00 (2006.01)
A61B 3/103 (2006.01)
A61B 3/113 (2006.01)
G06F 1/16 (2006.01)
G09G 3/00 (2006.01)

(52) U.S. Cl.
CPC ............ *G06F 3/013* (2013.01); *A61B 3/0025* (2013.01); *A61B 3/103* (2013.01); *A61B 3/113* (2013.01); *G06F 1/163* (2013.01); *G09G 3/003* (2013.01); *G09G 2320/0626* (2013.01); *G09G 2320/066* (2013.01); *G09G 2340/045* (2013.01); *G09G 2354/00* (2013.01)

(58) Field of Classification Search
None
See application file for complete search history.

(56) References Cited

U.S. PATENT DOCUMENTS

2019/0385342 A1* 12/2019 Freeman ................ G06T 11/00
2020/0124852 A1* 4/2020 Zhou ..................... G02C 7/081
2021/0034147 A1* 2/2021 Gadge ................. G09B 21/008
2021/0330185 A1* 10/2021 Krukowski ........ G02B 26/0833

* cited by examiner

Primary Examiner — Stephen T. Reed
(74) Attorney, Agent, or Firm — Baker Botts L.L.P.

(57) ABSTRACT

A method for compensating for a visual impairment in a virtual reality environment, by multiple computer systems associated with a head mounted display, including, rendering an initial image for display in a virtual reality environment, determining a first visual adjustment to the HMD based on an input received by the HMD, the input being associated with a visual impairment of a user of the HMD, determining that the first visual adjustment does not satisfy a threshold measure of compensation for the visual impairment of the user, determining a second visual adjustment to the HMD, and rendering an adjusted image for display in the virtual reality environment based on the first visual adjustment and the second visual adjustment.

20 Claims, 21 Drawing Sheets

HEAD MOUNTED DISPLAY WITH VISUAL CONDITION COMPENSATION

PRIORITY

This application is a continuation under 35 U.S.C. § 120 of U.S. patent application Ser. No. 18/185,254, filed 16 Mar. 2023, which claims the benefit under 35 U.S.C. § 119(c) of U.S. Provisional Patent Application No. 63/397,500, filed 12 Aug. 2022, which are incorporated herein by reference.

TECHNICAL FIELD

This disclosure generally relates to the field of medical devices and methods, and in particular relates to devices and methods for compensating for visual impairments while using a head-mounted display.

BACKGROUND

Virtual reality (VR) strives to create an immersive virtual world that generates the perception of being physically present in the VR environment. Immersion depends on surrounding the player with believable images, sounds, and other stimuli. Believable, life-like stimuli elicit a state of consciousness featuring a partial or complete suspension of disbelief that enables action and reaction to stimulations in the VR environment. An immersive VR system may include digital hardware and a software medical device platform, which may be used in combination to create a virtual environment, including full presence tracked avatars for visual feedback.

VR systems have been used in various applications, including games, and referenced herein may be used in therapeutic regimens to assist patients with their recovery from illness or injury. VR systems may be designed for use in healthcare and may be focused on physical rehabilitation and neurorehabilitation. As an example and not by way of limitation, victims of stroke or brain injury may go through physical therapy for treatment to improve, for example, range of motion, balance, coordination, joint mobility, flexibility, posture, endurance, and strength. Physical therapy may also help with pain management. Physical therapy may be a vital part of patients' recovery and achieving their goals of performing everyday life functions. VR systems may be used to entertain and instruct patients in their movements while facilitating practical exercises that may further patients' therapeutic goals.

Patient movement data captured during physical therapy sessions may be valuable to both patients and healthcare practitioners. Using sensors in VR implementations of therapy may allow for a deeper immersion as the sensors can capture movements of body parts, such as hands and arms, and the sensor data may be used to animate a character in the VR environment. Such an approach may approximate the movements of a patient to a high degree of accuracy. Advanced systems may include multiple sensors, which may allow for more accurate animated movements that mimic the patient's movements, which may in turn permit the patient to more accurately receive and observe feedback during VR activities. An important consideration may be that data from multiple sensors may be used to produce statistical feedback for viewing and analysis by doctors and therapists. There exists a need to convert motion of body parts in the real world to a VR world while preserving the proportionality and accuracy of position and orientation data for real-world data collection and analysis. Further, approaches utilizing multiple sensors may give rise to issues associated with, for example, sensor portability, sensor placement on the body, and general issues with sensor setup, among other potential problems. As an example and not by way of limitation, sensors may be placed on a patient's body indiscriminately and upside-down or backwards. There exists a need to simplify sensor placement and/or resolve inverted sensor data in order to reduce the need for human intervention and potential causes of errors.

Various systems and methods disclosed herein are described in the context of a therapeutic system for helping patients, such as stroke victims, but this application is only illustrative. In the context of the VR system, the word "patient" may be considered equivalent to a user or subject, and the term "therapist" may be considered equivalent to a doctor, physical therapist, supervisor, or any non-participating operator of the system. Particular embodiments include digital hardware and software for a medical device that uses VR for healthcare, focusing on physical and neuro rehabilitation. The device may be used in a clinical environment under the supervision of a medical professional trained in rehabilitation therapy. In particular embodiments, the device may be configured for personal use at home. In particular embodiments, a therapist or supervisor may monitor the patient's use of the device, and may do so in the same room or remotely. As an example and not by way of limitation, particular implementations may only require a remote therapist, while others may require both a remote therapist and someone physically present to assist the patient with properly placing or mounting the sensors and headset. In particular embodiments, the systems may be portable and may be readily stored and carried by, for example, a therapist visiting a patient.

With the rapid advances in VR technologies and the expanded usage of therapeutic VR, users have increased, many of whom have visual impairments. Visual impairments (such as nearsightedness, farsightedness, and astigmatism) may cause users to provide inaccurate responses to rendered VR images, and may make it difficult for users to interact with the VR environment. With the current design of most head-mounted displays (HMD) in the market, there may be sufficient additional space inside an HMD to enable users with visual impairments to wear optical glasses in the HMD to compensate for their visual impairment while observing the VR environment. However, wearing glasses in an HMD may influence the user's immersive VR experience and may prevent patients from completing therapeutic tasks in the VR environment, which in turn may significantly affect the outcome of the patient's therapy and treatment. For example, users with glasses may feel uncomfortable interacting with the VR (e.g., using body movements), and may not be able to respond quickly to a visual stimulus rendered in the VR environment. In another example, wearing glasses inside the HMD may interfere with tracking the user's eye gaze, for example, in the circumstance where the user may be looking from a particular angle that cannot be tracked through a camera of the HMD due to the user's glasses.

SUMMARY OF PARTICULAR EMBODIMENTS

The present disclosure provides systems and methods that compensate for users' visual impairments while using a head-mounted display (HMD) by automatically adjusting rendered images, automatically adjusting optical lenses of the HMD, or both. Such adjustments may enhance users' VR experiences and leverage benefits for patients with visual impairments using therapeutical VR applications for post-illness or post-injury treatment.

In particular embodiments, computer systems associated with the HMD may render an image for display in a VR environment (e.g., through GPU rendering), wherein the rendered image may be of a standard image quality such that the HMD may enable users without visual impairments to see the rendered image clearly and experience the rendered VR environment immersively. Users without visual impairments may be users who have 20/20-vision without astigmatism. The computer systems may identify a visual impairment associated with a user of the HMD based at least in part on an input received by the HMD, wherein the input received by the HMD is provided by the user wearing the HMD. The computer system may determine visual adjustments to the HMD based on the identified visual impairment associated with the user. The visual adjustments may comprise adjustments to the rendered image displayed in the HMD. Additionally or alternatively, the visual adjustments may comprise adjustments to the optical lenses of the HMD. Based on the determined visual adjustments, the computer systems may render an adjusted image for display in the VR environment. The adjusted rendered image may compensate for the user's identified visual impairments and enable the HMD to satisfy visual requirements for different users with different visual conditions. In particular embodiments, the visual impairment identified by the computer system associated with the HMD may comprise one or more of nearsightedness, farsightedness, and an astigmatism.

In particular embodiments, the input received by the HMD may comprise one or more user inputs received by the HMD, wherein the user inputs may comprise one or more eye positions detected by the HMD. The user inputs may be further based on a detection of one or more eye movements based on the one or more detected eye positions. The user inputs may be further based on a focal point based on the one or more detected eye positions. The detected one or more eye positions may be associated with a visual prompt displayed in the VR environment. The eye movements and focal point may indicate the present visual conditions of the user. In particular embodiments, the system may compare one or more detected eye positions to one or more reference eye positions. The reference eye positions may be predetermined based on a user without visual impairments (i.e., 20/20-vision without astigmatism). Subsequent to the comparison, the system may identify the visual impairment based on the comparison of the detected eye positions and the reference eye positions. The HMD may comprise a camera to detect the eye positions and perform eye gaze tracking while VR content is being displayed to the user.

In particular embodiments, the input received by the HMD may comprise one or more user inputs received by the HMD, wherein the user inputs may comprise one or more audio commands detected by the HMD. The user may provide an audio command in response to a rendered image or in response to a visual prompt, which may be configured to test the visual conditions of the user. The system may determine visual adjustments to the HMD based on the audio command. The user may provide the HMD with the audio command through an audio interface. The audio command may be parsed by a natural language processor of the computer systems associated with the HMD to determine an intent of the user to compensate for a visual impairment.

In particular embodiments, the input received by the HMD may comprise one or more user inputs received by the HMD, wherein the user inputs may comprise one or more body movements detected by the HMD. The HMD may detect body movements through one or more sensors placed on the user's body. The user may provide such body movements in response to a rendered image or in response to a visual prompt, which may be configured to test the visual conditions of the user. For example, the user may use gestures to respond to visual prompts that include a moving object or to make a selection according to the displayed image. The system may determine visual adjustments to the HMD based on the user's body movements.

In particular embodiments, the computer system associated with the HMD may detect more than one input such as eye positions, audio commands, and body movements, which may be detected by more than one interface (e.g., eye gaze tracking interface, audio input interface, body movement sensors, ophthalmology, and optometry sensors) of the HMD, and the multiple inputs may be detected at the same time or within a period of time. The computer system may synthesize all types of inputs received by the HMD and may determine adjustments based on the synthesized inputs, which may indicate the need to compensate for the user's visual impairment.

In particular embodiments, one or more of the visual adjustments to the HMD may comprise one or more adjustments to the image displayed in the VR environment. For example, and not by way of limitation, adjustments to the image may comprise an adjustment to an image zoom, an image perspective, an image brightness, an image sharpness, and/or an image contrast in order to compensate for the user's visual impairment based on the user inputs. In particular embodiments, one or more of the visual adjustments to the HMD may comprise one or more adjustments to one or more optical lenses of the HMD. Adjustments to the optical lenses may be associated with adjustments to an imaging focal length. In particular embodiments, the HMD may comprise a pair of optical lenses or a greater number of optical lenses. In particular embodiments, adjustments to the optical lenses of the HMD may comprise altering a position of one or more optical lenses. In particular embodiments, adjustments to the optical lenses of the HMD may comprise altering a shape of one or more optical lenses, wherein altering the shape of the optical lenses may comprise altering a curvature of the optical lenses to modify the imaging focal length. In particular embodiments, adjustments to the optical lenses of the HMD may comprise altering an index of refraction of one or more optical lenses.

In particular embodiments, the computer systems may further determine one or more second visual adjustments to the HMD based on the identified visual impairment and one or more second inputs received by the HMD, wherein the one or more second inputs may be received in response to the adjusted image displayed in the VR environment, and the one or more second visual adjustments may correspond to a measure of compensation for the visual impairment, wherein the second visual adjustments may be associated with a second adjusted image. For example, and not by way of limitation, the computer systems may recalibrate images after the visual adjustments for the user with visual impairment after a particular time duration (e.g., 5 minutes) and/or for distinct VR programs that require different visual capabilities. In particular embodiments, the computer system associated with the HMD may first perform adjustments to the optical lenses of the HMD based on the visual impairment identified based on the user inputs. The adjustments to the optical lenses may have limitations (e.g., the optical lenses may be capable of compensating for nearsightedness with moderate myopia no greater than −5.00 D) and the first visual adjustments may not sufficiently compensate for the user's visual impairment. The system may further determine adjustments to the rendered images and/or adjustments to further compensate for the user's visual impairment.

The embodiments disclosed herein are only examples, and the scope of this disclosure is not limited by such examples. Particular embodiments may include all, some, or none of the components, elements, features, functions, operations, or steps of the embodiments disclosed herein. Particular embodiments according to the present disclosure are recited in the attached claims directed to a method, a storage medium, a system and a computer program product, wherein any feature mentioned in one claim category, e.g., method, can be claimed in another claim category, e.g., system, as well. The dependencies or references back in the attached claims are chosen for formal reasons only. However, any subject matter resulting from a deliberate reference back to any previous claims (in particular multiple dependencies) can be claimed as well, so that any combination of claims and the features thereof are disclosed and can be claimed regardless of the dependencies chosen in the attached claims. The subject-matter which can be claimed comprises not only the combinations of features as set out in the attached claims but also any other combination of features in the claims, wherein each feature mentioned in the claims can be combined with any other feature or combination of other features in the claims. Furthermore, any of the embodiments and features described or depicted herein can be claimed in a separate claim and/or in any combination with any embodiment or feature described or depicted herein or with any of the features of the attached claims.

DESCRIPTION OF EXAMPLE EMBODIMENTS

Particular embodiments as disclosed in the present application are described below. For clarity, not all features of each actual implementation are described in this specification. In the development of an actual device, particular modifications may be made that result in an embodiment that still falls within the scope of the present disclosure.

Figure 1:
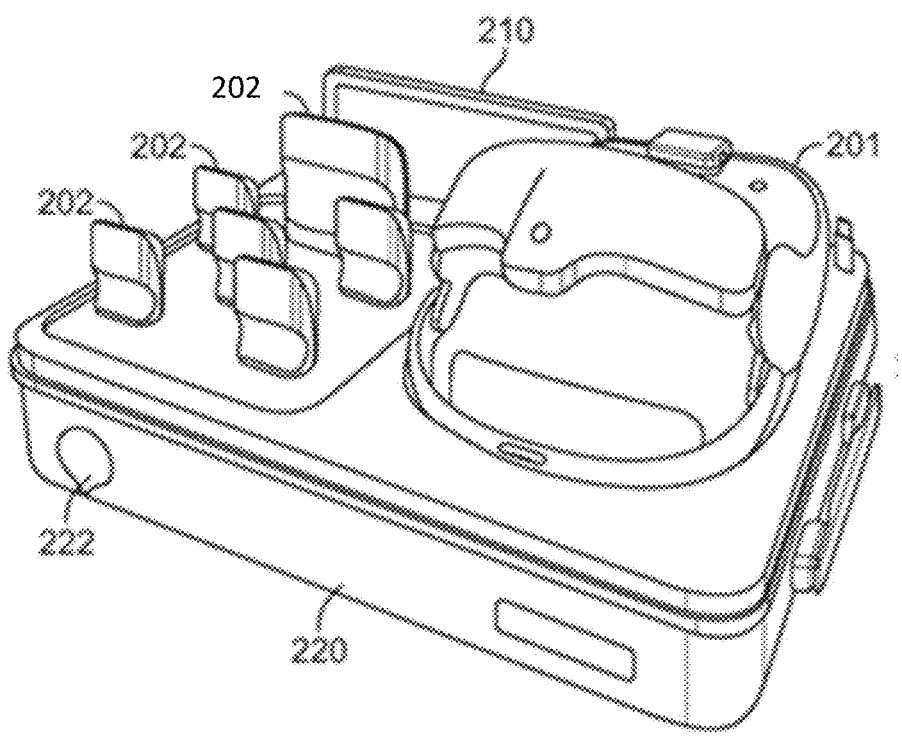
FIG. 1 is a diagram of an illustrative system and case, in accordance with particular embodiments of the disclosure.

FIG. 1 is a diagram of an illustrative system and case, in accordance with particular embodiments of the disclosure. As an example and not by way of limitation, a VR system may include a clinician tablet 210, head-mounted display (HMD or headset) 201, sensors 202, charging dock 220, a router, a router battery, headset controller, power cords, and USB cables.

The clinician tablet 210 may be configured to use a touch screen, a power/lock button that turns the component on or off, and a charger/accessory port, e.g., USB-C. As an example and not by way of limitation, pressing the power button may power on or restart the clinician tablet 210. Once powered on, a clinician may access a user interface, which may enable the clinician to log in, add or select a patient, initialize and sync sensors, select, start, modify, or end a therapy session, view data, and log out.

A headset 201 may contain a power button that turns the component on or off, as well as a charger/accessory port, e.g., USB-C. The headset also provides visual feedback of VR applications in concert with the clinician tablet 210 and the small and large sensors. HMD 201 may include one or more sensors 202. HMD 201 may include a wireless receiver, which may be positioned on or near the headset sensor 202, and may be configured to receive position and orientation data from sensors 202 transmitted wirelessly via, e.g., 2.4 GHz radio frequency. As an example and not by way of limitation, each sensor may communicate, via radio frequency, its position and orientation to the HMD receiver every few milliseconds.

Charging the headset 201 may be performed by plugging a headset power cord into the storage dock 220 or an outlet. To turn on headset or restart headset, the power button may be pressed. A power button may be on top of the headset. Particular embodiments may include a headset controller used to access system settings. As an example and not by way of limitation, a headset controller may be configured for use in particular troubleshooting and administrative tasks. Buttons on the controller may be used to control power, connect to headset, access settings, or control volume.

The sensors 202 may be equipped with mechanical and electrical components that measure position and orientation in physical space, and then translate that information to construct a VR environment. In particular embodiments, wearable sensors 202 may be comprised of electromagnetic receivers and emitters, one or more optical elements, infrared emitters, accelerometers, magnetometers, gyroscopes, or a combination thereof. In particular embodiments, the processor may receive tracking data from both electromagnetic sensors and one or more cameras. In particular embodiments, the wearable sensors 202 may be wireless and communicate with the HMD and/or other components via radio frequency.

As an example and not by way of limitation, a VR system may comprise one or more electromagnetic emitters and one or more electromagnetic sensors configured to be selectively placed on one or more tracked body parts. Processing circuitry may be in communication with the sensors, emitters, and a visual display such as HMD 201, and the processing circuitry may be configured to receive tracking data from one or more electromagnetic emitters and the one or more electromagnetic sensors 202, and may be further configured to generate complementary display data comprising, e.g., an avatar in the VR environment that may appear to move according to sensor data. HMD 201 may include a wireless receiver, which may be positioned on or near the headset sensor 202, and may be configured to receive position and orientation data from sensors 202 wirelessly via radio frequency. In particular embodiments, wireless communications may utilize an integrated low-power RF system-on-a-chip and/or a 2.4-GHz RF protocol stack. As an example and not by way of limitation, each sensor 202 (and a wireless transmitter module) may communicate, via radio frequency, its position and orientation to the HMD receiver every few milliseconds (e.g., 4 ms).

Sensors 202 may be turned off and charged when placed in charging station 220. Sensors 202 may turn on and attempt to sync when removed from the charging station. The charging station 220 may act as a dock to store and charge the sensors 202, clinician tablet 210 and/or headset 201. In particular embodiments, sensors 202 may be placed in sensor bands 205 on a patient. Sensor bands 205 may be required for use and may be provided separately for each patient for hygienic purposes. In particular embodiments, sensors 202 may be miniaturized, and may be placed, mounted, fastened, or pasted directly onto the user.

As shown in illustrative FIG. 1, various systems disclosed herein comprise a set of position and orientation sensors that may be worn by a VR participant, which may be, for example, a patient. These sensors, e.g., sensors 202, may communicate with an HMD 201, which may be configured to immerse the user in a VR experience. An HMD 201 suitable for VR may comprise one or more displays to enable the display of stereoscopic three-dimensional ("3D") images. Such internal displays may be high-resolution (e.g., 2880×1600 or better) and may operate at a high refresh rate (e.g., 75 Hz). The displays may be configured to present three dimensional images to the user. HMD 201 may include speakers and microphones for deeper immersion.

HMD 201 may be a central piece to immersing a user in a VR environment in terms of presentation and movement. As an example and not by way of limitation, HMD 201 may allow for a wide field of view (e.g., 110°) and tracking along six degrees of freedom. HMD 201 may include cameras, accelerometers, gyroscopes, and proximity sensors. HMD 201 may include a processor, which may be in the form of a system on a chip (SoC), and memory. HMD 201 may use additional cameras as safety features to help users avoid real-world obstacles. HMD 201 may comprise multiple connectivity options, which may enable HMD 201 to communicate with the clinician tablet 210. As an example and not by way of limitation, HMD 201 may use an SoC that features WiFi, Bluetooth, and/or other radio frequency connectivity, which may be in addition to an available USB connection (e.g., USB Type-C). The USB-C connection may be used to charge the built-in rechargeable battery for the headset.

A healthcare provider may use the clinician tablet 210 depicted in FIG. 1 to control the experience of a user, e.g., a patient. The tablet may run an application and communicate with a router to cloud software configured to authenticate users and store information. Clinician tablet 210 may communicate with HMD 201 in order to initiate HMD applications, collect relayed sensor data, and update records on the cloud servers. Clinician tablet 210 may be stored in the portable container and may be plugged in to charge via a USB plug.

Figure 2A:
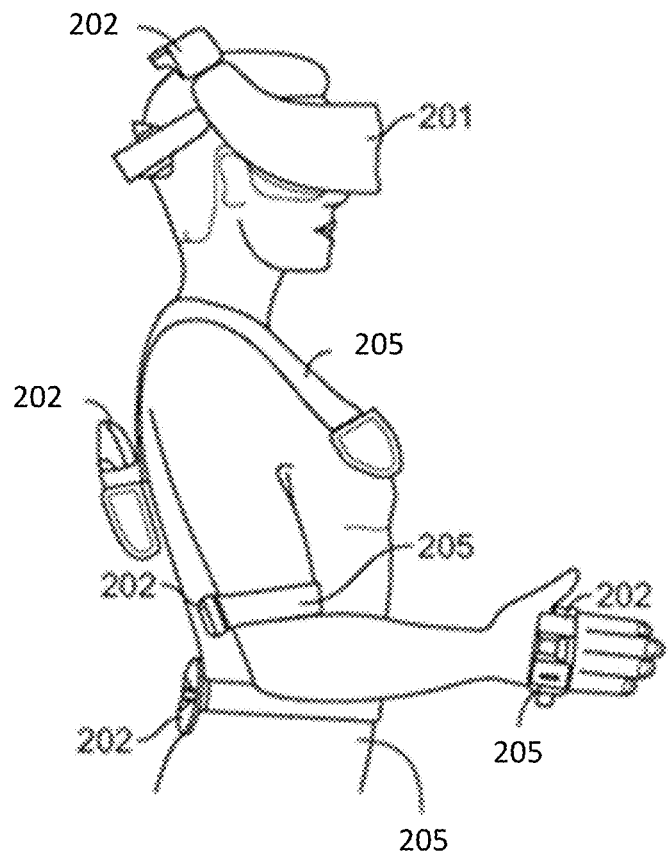
FIG. 2A is a diagram depicting a side view of an illustrative system placed on a participant, in accordance with particular embodiments of the disclosure.
Figure 2B:
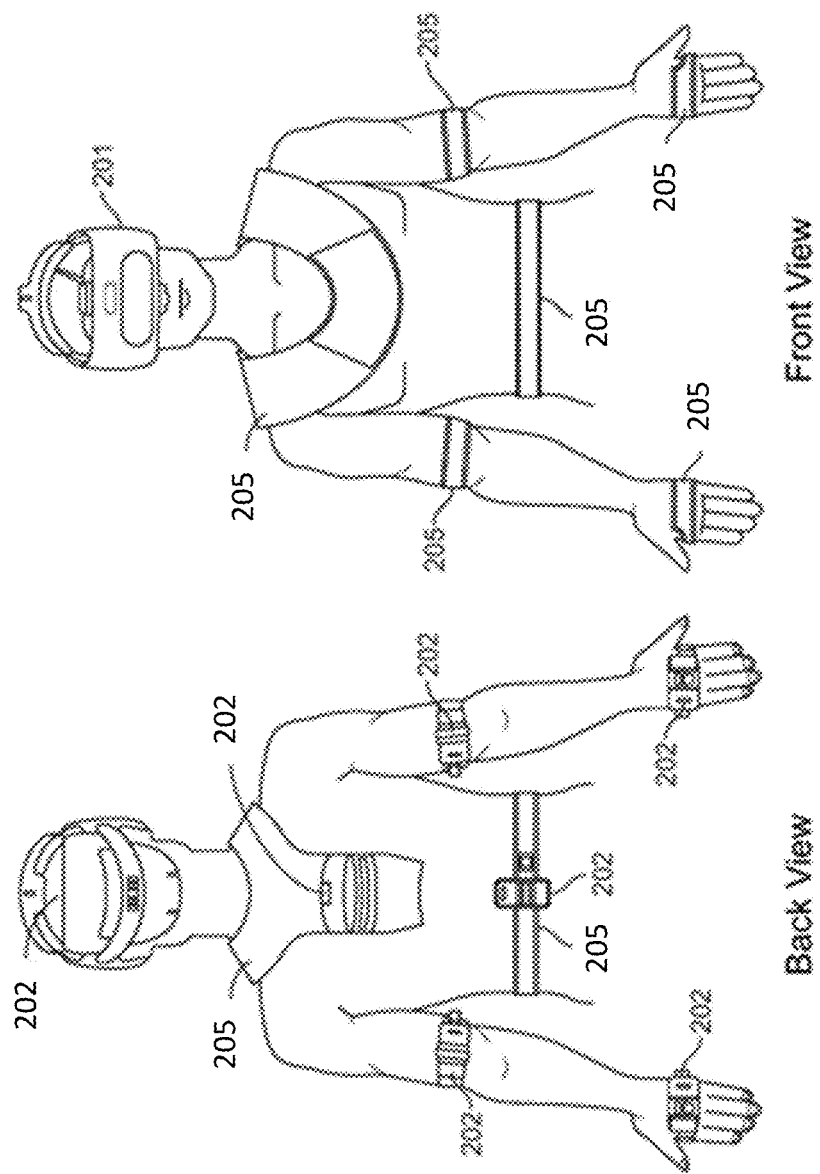
FIG. 2B are diagrams depicting front and back views of an illustrative system placed on a participant, in accordance with particular embodiments of the disclosure.

FIG. 2A is a diagram depicting a side view of an illustrative system placed on a user, in accordance with particular embodiments of the disclosure. FIG. 2B are diagrams depicting front and back views of an illustrative system placed on a user, in accordance with particular embodiments of the disclosure. In particular embodiments, such as depicted in FIGS. 2A-2B, sensors 202 may be placed on the user's body in particular places to measure body movement and relay the measurements for translation and animation of a VR avatar. Sensors 202 may be strapped to a user's body via bands 205. In particular embodiments, each user may have their own set of bands 205 to minimize hygiene issues.

A wireless transmitter module (WTM) may be worn on a sensor band 205 laid over the user's shoulders. The WTM may sit between the user's shoulders on their back. In particular embodiments, the WTM may include a sensor 202. In particular embodiments, the WTM may transmit its position data in relation to one or more sensors 202 and/or the HMD 201. In particular embodiments, the WTM may emit an electromagnetic field (EMF), and sensors 202 may be wearable electromagnetic (EM) sensors. For example, wearable sensor 202 may include an EM receiver and a wireless transmitter.

Each sensor 202 may learn its position and orientation relative to the WTM, e.g., via calibration. Sensors 202 with EM receivers in an EMF may provide precise position and orientation tracking with fidelity and precision down to, e.g., the nearest 1 mm (position) and degree (orientation). In particular embodiments, wearable sensor 202 may use EMF and inertial measurement. Wireless sensor modules 202 (e.g., sensors or WSMs) may be worn just above each elbow, strapped to the back of each hand, and/or on a pelvis band that positions a sensor adjacent to the user's sacrum on their back. Wearable sensors 202 may include a light indicating charge status, which may display colors such as blue or green to indicate that it is charged or charging, and red to indicate that charging is needed. Wearable sensors 202 may be wireless, small, and nonintrusive as illustrated in FIGS. 4-8. In particular embodiments, each WSM may communicate its position and orientation data in real-time to an HMD Accessory (e.g., HMD receiver) of the HMD 201.

Figure 3:
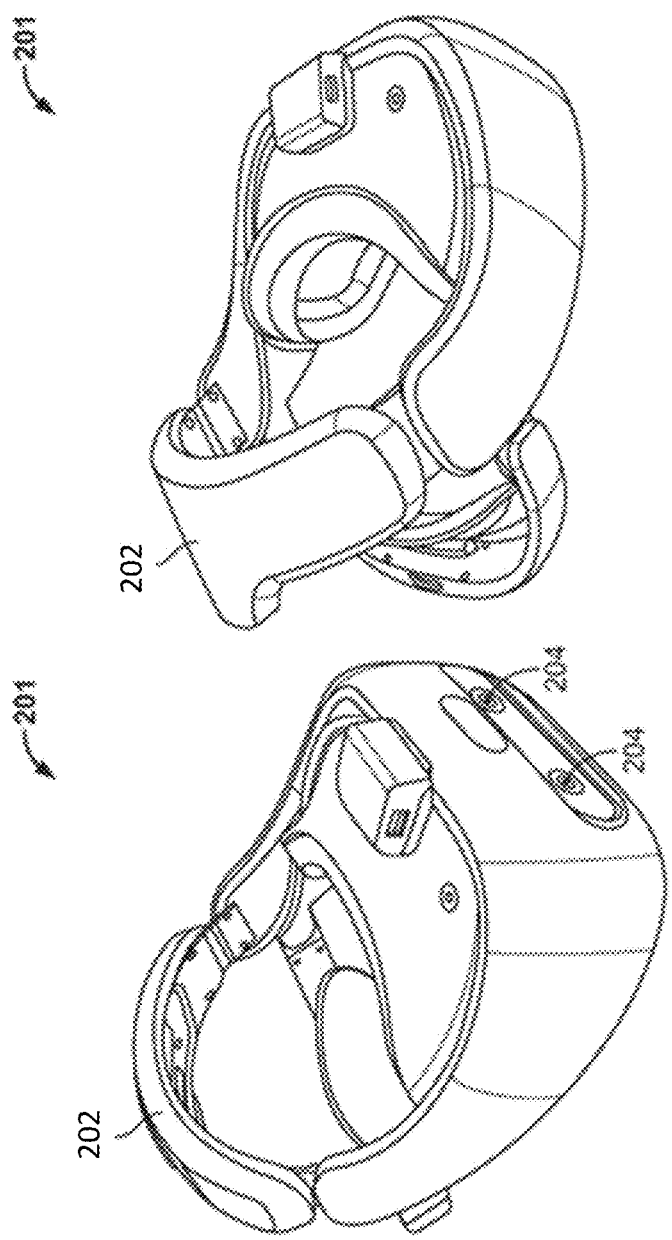
FIG. 3 is a diagram of a head-mounted display of an illustrative system, in accordance with particular embodiments of the disclosure.

FIG. 3 is a diagram of an HMD of an illustrative system, in accordance with particular embodiments of the disclosure. An HMD Accessory may include a sensor 202 that may allow it to learn its position and orientation relative to a WTM. The HMD Accessory may include a wireless receiver which allows the HMD 201 to know where in physical space all the WSMs and WTM are located. The HMD Accessory receiver may utilize an integrated low-power RF system-on-a-chip and/or a 2.4-GHz RF protocol stack to communicate wirelessly. In particular embodiments, each of sensors 202 may communicate independently with the HMD Accessory, which may then transmit data to the HMD 201, e.g., via a USB-C connection. In particular embodiments, each sensor 202 may learn its position and orientation (P&O) based on the ElVlF emitted by WTM (and other sensor data) and each sensor 202 may wirelessly communicate the P&O data with HMD 201, e.g., via radio frequency.

Figure 4:
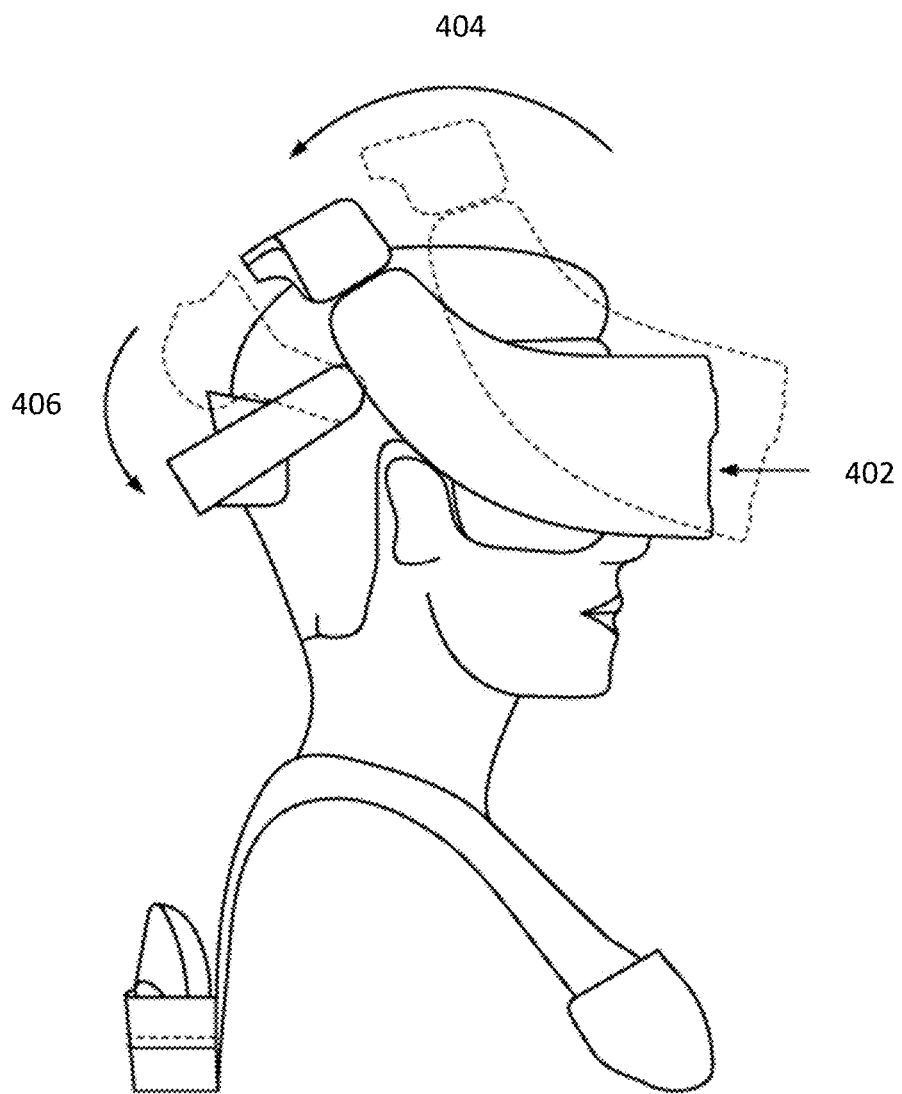
FIG. 4 is a diagram of a head-mounted display of an illustrative system placed on a participant's head, in accordance with particular embodiments of the disclosure.

A user may wear HMD 201 on their head and over their face. FIG. 4 is a diagram illustrating placement of HMD 201 of an illustrative system on a user's (e.g., a therapy patient) head, in accordance with particular embodiments of the disclosure. Placement of an HMD 201 on a patient, may require the assistance of a therapist. HMD 201 may be adjustable to fit the patient's head comfortably. HMD 201 may be configured to adjust the interpupillary distance between the patient's eyes so that, for example, the displays line-up properly with the eyes in order to produce a three-dimensional view, while maintaining the user's comfort. While safety is important for patients and therapists during therapy, comfort may also be vital for the patient's engagement and success of the therapy.

In particular embodiments, a first step (A) may include lining up the front of HMD 201, including, e.g., lining up the visor with the patient's eyes and nose. A second step (B) may include pulling the top of the headset back. In particular embodiments, the top of the headset may include a wireless transmitter and sensor 202. Lastly, in step (C), the back of the headset may be placed on the back of the patient's head, and may be adjusted for secure fit and comfort. In particular embodiments, HMD 201 may include an adjustment dial to comfortably secure the headset on the patient.

Once HMD 201 is in place and turned on, a patient may begin to explore a VR environment. A VR environment rendering engine on HMD 201 (sometimes referred to herein as a "VR application"), such as the Unreal® Engine, may use the position and orientation data to generate a VR environment including a virtual avatar that mimics the patient's movement and view. Unreal Engine is a software-development environment with a suite of developer tools designed for developers to build real-time 3D video games, virtual and augmented reality graphics, immersive technology simulations, 3D videos, digital interface platforms, and other computer-generated graphics and worlds. A VR application may incorporate the Unreal Engine or another three-dimensional environment developing platform, (sometimes referred to as a VR engine or a game engine). Particular embodiments may utilize a VR application, stored and executed by one or more of the processors and memory of a headset, server, tablet and/or other device to render Scenario 100. As an example and not by way of limitation, a VR application may be incorporated in one or more of HMD 201, clinician tablet 210, and/or the systems of FIGS. 9-10.

A patient may "become" their avatar when they login or enter into a VR game, exercise, or environment. When the patient moves their body, they may see their virtual avatar move accordingly. Sensors in HMD 201 may allow the patient to move their virtual avatar's head even before or without body sensors placed on the patient. If a system achieves consistent high-quality tracking, then the patient's movements may be accurately and comprehensively mapped onto their virtual avatar, which may thereby enable deeper immersion in the VR environment.

HMD 201 may be essential for immersing a patient in the sights (and head movements) of a VR environment, and sensors 202 may be essential to replicating the real-world movement of body parts below the patient's neck in the VR world. Sensors 202 may be placed on the body of a patient by a therapist, and may be placed in particular locations to sense and/or translate body movements. HMD 201 may use measurements of position and orientation of sensors 202 placed in key places to determine movement of the patient's body parts in the real world and translate such movement to the VR environment, and may additionally collect data for therapeutic analysis of a patient's range of motion.

FIGS. 5A-8 illustrate examples of wearable sensors 202 and bands 205. To attach sensors 202, the sensors 202 may include a recess that accommodates a cloth and Velcro band 205 that may be used to attach wearable sensors 202 to a patient. In particular embodiments, bands 205 may include elastic loops to hold the sensors 202. This attachment method beneficially does not require the patient to physically hold anything, and may leave the hands of the patient free during performance of therapeutic exercises. Therapeutic exercises may be performed more easily when a patient does not have to physically hold a controller, and when the patient is not attached by wiring. In particular embodiments, bands 205 may include additional loops, buckles and/or Velcro straps to hold the sensors 202. As an example and not by way of limitation, bands 205 for the patient's hands may need to be secured to a greater degree than other sensors 202 because a patient's hands may move at a greater speed than other body parts, which may result in the hand sensor 202 being thrown or projected if it is not securely fastened.

Figure 5A:
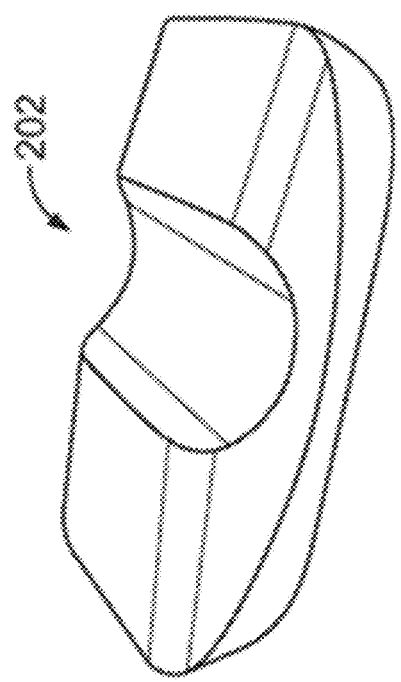
FIG. 5A is a diagram of a sensor an illustrative system, in accordance with particular embodiments of the disclosure.
Figure 5B:
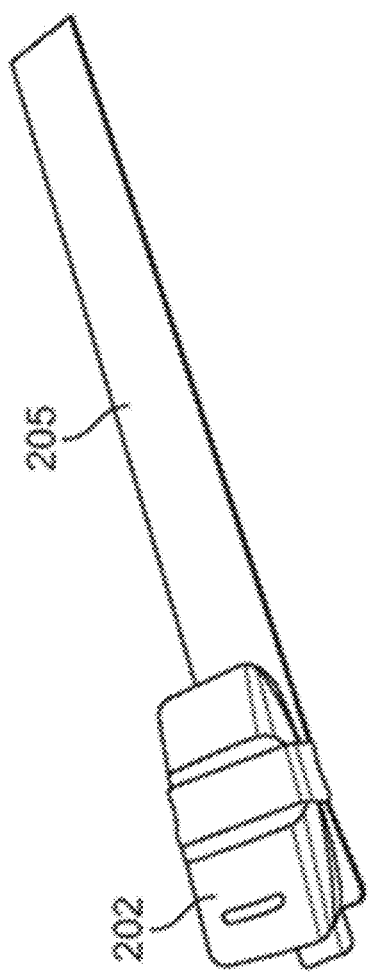
FIG. 5B is a diagram of a sensor band of an illustrative system, in accordance with particular embodiments of the disclosure.
Figure 6A:
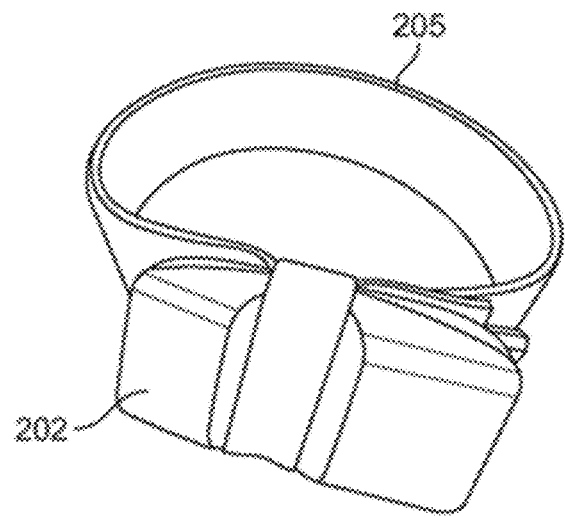
FIG. 6A is a diagram of a sensor placed in a sensor band of an illustrative system, in accordance with particular embodiments of the disclosure.
Figure 6B:
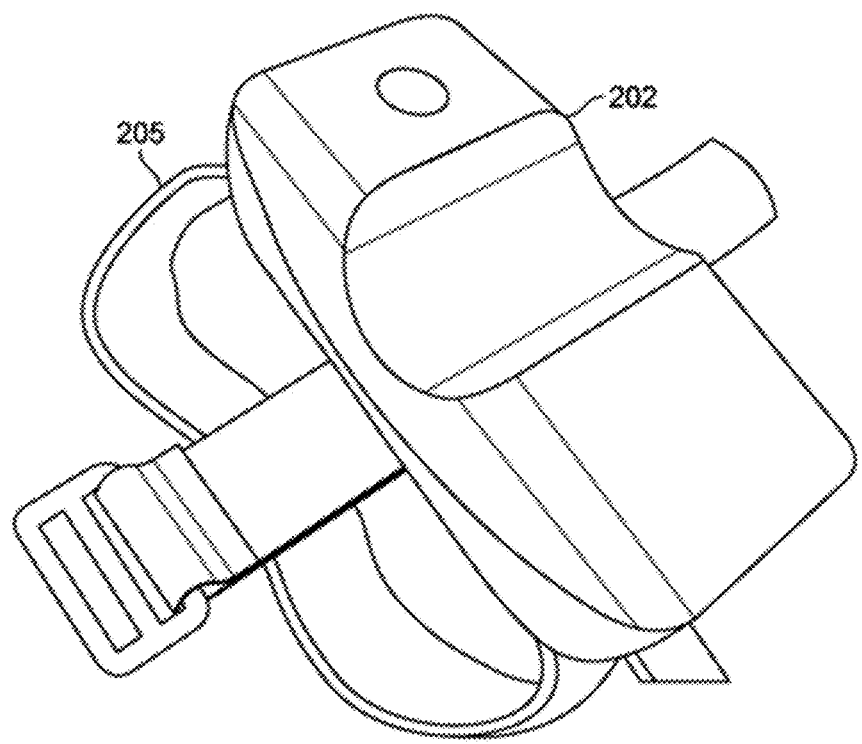
FIG. 6B is a diagram of a sensor placed in a sensor band of an illustrative system, in accordance with particular embodiments of the disclosure.

FIG. 5A is a diagram of a sensor 202 of an illustrative system, in accordance with particular embodiments of the disclosure. FIG. 5B is a diagram of a sensor band 205 of an illustrative system, in accordance with particular embodiments of the disclosure. FIGS. 6A-6B show a diagram of a sensor 202 placed in a sensor band 205 of an illustrative system, in accordance with particular embodiments of the disclosure. In particular embodiments, systems and methods of the present disclosure may use electromagnetic tracking, optical tracking, infrared tracking, accelerometers, magnetometers, gyroscopes, myoelectric tracking, inertial measuring unit, other tracking techniques, or a combination of one or more of such tracking methods. The tracking systems may be parts of a computing system as disclosed herein. The tracking tools may exist on one or more circuit boards within the VR system (see FIGS. 9-10), where they may monitor one or more users to perform one or more functions such as capturing, analyzing, and/or tracking a user's movements. In particular cases, the VR system may utilize more than one tracking method to improve reliability, accuracy, and precision. FIG. 6B illustrates an exemplary embodiment with a slide buckle.

Figure 7:
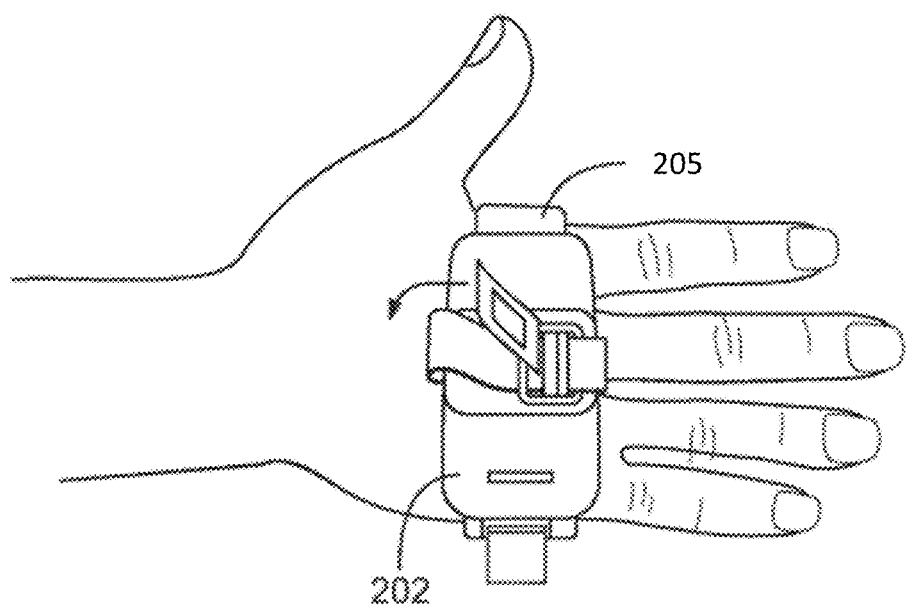
FIG. 7 is a diagram of a sensor and sensor band of an illustrative system placed on a participant's hand, in accordance with particular embodiments of the disclosure.

FIG. 7 is a diagram a sensor 202 of an illustrative system placed in a sensor band 205 that is placed on a user's hand, in accordance with particular embodiments of the disclosure. In particular embodiments, sensor bands 205 may have one or more buckles to fasten sensor 202 more securely. As an example and not by way of limitation, the hand sensor band 205 of FIG. 7 features a buckle to facilitate fastening sensor 202 more securely. Each of sensors 202 may be placed at any suitable location, e.g., as depicted in FIG. 2B. After sensors 202 have been placed on the body they may be assigned or calibrated for each corresponding body part. Generally, sensor assignment may be based on the position of each sensor 202. In particular cases, patients may have varying height discrepancies such that assigning a sensor 202 based on height is not practical or effective. In particular embodiments, sensor assignment may be based on a relative position to, e.g., wireless transmitter module.

Figure 8:
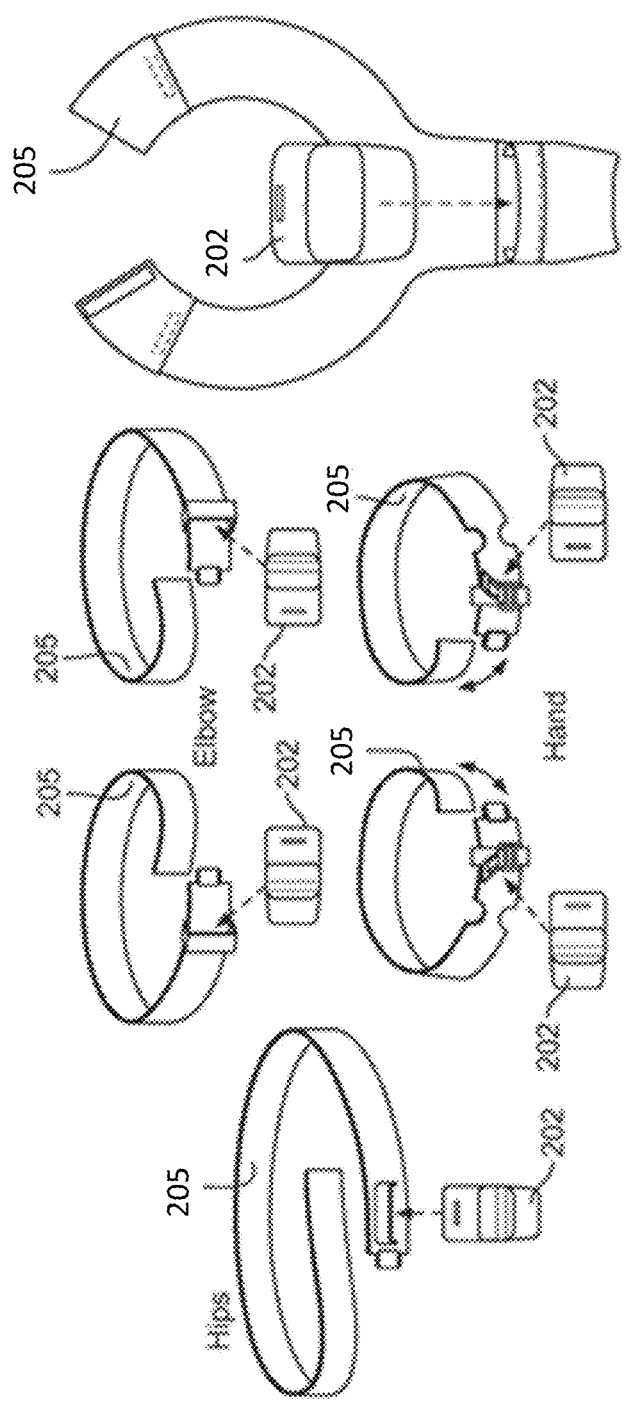
FIG. 8 is a diagram of a sensor and sensor band of an illustrative system, in accordance with particular embodiments of the disclosure.

FIG. 8 is a diagram of sensors 202 and sensor bands 205 of an illustrative system, in accordance with particular embodiments of the disclosure. Sensors 202 may be attached to body parts via band 205. In particular embodiments, a therapist attaches sensors 202 to appropriate areas of a patient's body. For example, a patient may not be physically able to attach band 205 to themself. In particular embodiments, each patient may have their own set of bands 205 to minimize hygiene issues. In particular embodiments, a therapist may bring a portable case to a patient's room or home for therapy. The sensors 202 may include contact ports for charging each sensor's battery while being stored and transported in the case, e.g., as depicted in FIG. 1.

As illustrated in FIGS. 6B and 8, sensors 202 may be placed in bands 205 prior to placement on a patient. In particular embodiments, sensors 202 may be placed onto bands 205 by sliding them into elasticized loops. A large sensor, WTM 202, may be placed into a pocket of shoulder band 205. Sensors 202 may be placed above the elbows, on the back of the hands, and at the lower back (sacrum). In particular embodiments, sensors 202 may be placed at the knees and/or ankles. Sensors 202 may be placed, e.g., by a therapist, on a patient while the patient is sitting on a bench (or chair) with his hands on his knees. Sensor band 205 may be used with a hip sensor 202 and may have sufficient length to encircle a patient's waist.

Once sensors 202 are placed in bands 205, each band may be placed on a body part, e.g., according to placement of sensors depicted in FIG. 2B. In particular embodiments, shoulder band 205 may require connection using a hook and loop fastener. An elbow band 205 holding a sensor 202 may sit behind the patient's elbow.

Figure 9:
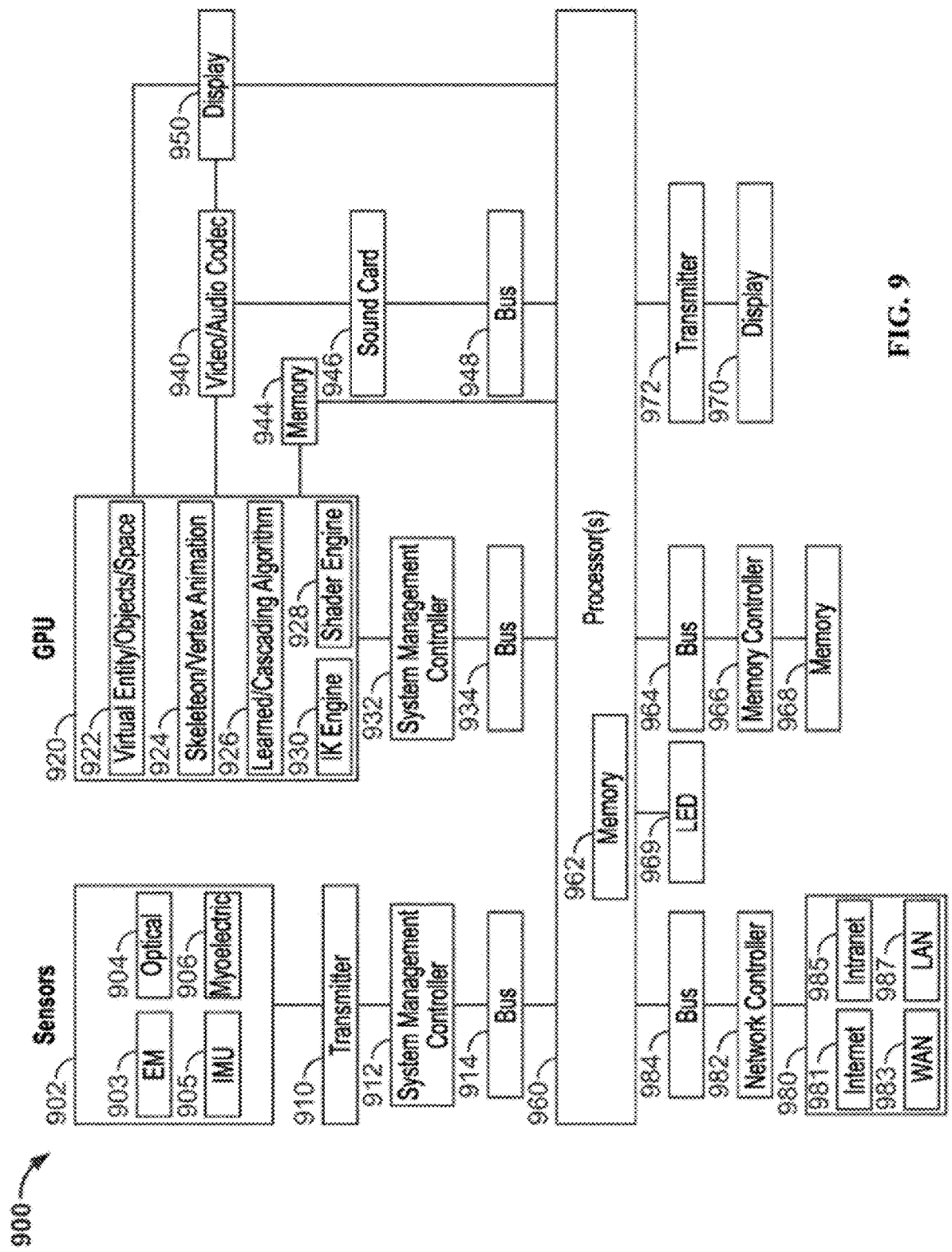
FIG. 9 is a diagram of an illustrative system, in accordance with particular embodiments of the disclosure.

FIG. 9 depicts an illustrative computing arrangement 900 for various elements of a system, e.g., an HMD 201 and sensors. The computing arrangement 900 may include one or more printed circuit boards (PCBs). In general terms, the elements of computing arrangement 900 may track, model, and display a VR environment and a visual representation of the participant (e.g., an avatar of the patient) in the VR environment by running software including the aforementioned VR application of HMD 201. The computing arrangement 900 shown in FIG. 9 may include one or more sensors 902, processors 960, graphic processing units (GPU) 920, video encoder/video codec 940, sound cards 946, transmitter modules 910, network interfaces 980, and lights emitting diodes (LED) 960. These components may be housed on a local computing system or may be remote components in wired or wireless connection with a local computing system (e.g., a remote server, a cloud, a mobile device, a connected device, etc.). Connections between the components may be facilitated by one or more buses (e.g., peripheral component interconnects (PCI) bus, PCI-Express bus, or universal serial bus (USB)), such as bus 914, bus 934, bus 948, bus 984, and bus 964. With such buses, the computing arrangement 900 may be capable of integrating numerous components, PCBs, and/or remote computing systems.

One or more system management controllers, such as system management controller 912 or system management controller 932, may provide data transmission management functions between the buses and the components they integrate. As an example and not by way of limitation, system management controller 912 may provide data transmission management functions between bus 914 and sensors 902. System management controller 932 may provide data transmission management functions between bus 934 and GPU 920. Such management controllers may facilitate the operation and arrangement of the components, which may each utilize separate instructions within defined time frames to execute applications. Network interface 980 may include an Ethernet connection and/or a component that forms a wireless connection, e.g., 802.11b, g, a, or n connection (WiFi), to a local area network (LAN) 987, wide area network (WAN) 983, intranet 985, or internet 981. Network controller 982 may provide data transmission management functions between bus 984 and network interface 980.

Processor(s) 960 and GPU 920 may execute particular instructions, such as, e.g., machine-readable instructions. The instructions may include instructions for receiving, storing, processing, and transmitting tracking data from various sources, such as electromagnetic (EM) sensors 903, optical sensors 904, infrared (IR) sensors, inertial measurement units (IMUs) sensors 905, and/or myoelectric sensors 906. The tracking data may be communicated to processor(s) 960 by a wired or wireless communication link, e.g., via transmitter 910. Upon receiving tracking data, processor(s) 960 may execute an instruction to permanently or temporarily store the tracking data in memory 962 as, e.g., random access memory (RAM), read only memory (ROM), cache, flash memory, hard disk, or any other suitable storage component. Memory 968 may be a separate component in communication with processor(s) 960 or may be integrated into processor(s) 960.

Processor(s) 960 may also execute instructions for constructing an instance of virtual space. The instance may be hosted on an external server and may persist and undergo changes even when a user is not logged into said instance. In particular embodiments, the instance may be user-specific, and the data required to construct it may be stored locally. In such an embodiment, new instance data may be distributed as updates that users download from an external source into local memory. In particular embodiments, the instance of virtual space may include a virtual volume of space, a virtual topography (e.g., ground, mountains, lakes), virtual objects, and virtual characters (e.g., non-player characters "NPCs"). The instance may be constructed and/or rendered in 2D or 3D. The rendering may offer the user a first-person or third-person perspective. A first-person perspective may include displaying the VR environment from the eyes of the avatar, and may allow the user (e.g., the patient) to view body movements from the avatar's perspective. A third-person perspective may include displaying the VR environment from behind or above the avatar to allow the user to view the avatar's body movements from a different perspective. The instance may include properties of physics, such as gravity, magnetism, mass, force, velocity, and acceleration, that may cause virtual objects in the virtual space to behave in a manner visually similar to the behavior of real objects in real space.

Processor(s) 960 may execute a program (e.g., the Unreal engine/application discussed above) for analyzing and modeling tracking data. As an example and not by way of limitation, processor(s) 960 may execute a program that analyzes the tracking data it receives according to algorithms described herein, along with other related pertinent mathematical formulas. Such a program may incorporate a graphics processing unit (GPU) 920 that may be capable of translating tracking data into 3D models. GPU 920 may utilize shader engine 928, vertex animation 924, and/or linear blend skinning algorithms. In particular instances, processor(s) 960 or a CPU may at least partially assist the GPU 920 in making such calculations. This may allow GPU 920 to dedicate more resources to the task of converting 3D scene data to the projected render buffer. GPU 920 may refine the 3D model by using one or more algorithms, such as an algorithm trained on biomechanical movements, a cascading algorithm that converges on a solution by parsing and incrementally considering multiple sources of tracking data, an inverse kinematics (IK) engine 930, a proportionality algorithm, and any other suitable algorithm related to data processing and animation techniques. After GPU 920 constructs a suitable 3D model, processor(s) 960 may execute a program to transmit data for the 3D model to another component of the computing arrangement 900, or to a peripheral component in communication with computing environment, that may be capable of displaying the model, such as display 950.

In particular embodiments, GPU 920 may transfer the 3D model to a video encoder or a video codec 940 via a bus, which may then transfer information representative of the 3D model to a suitable display 950. The 3D model may be representative of a virtual entity that can be displayed in an instance of virtual space, e.g., an avatar. The virtual entity may be capable of interacting with the virtual topography, virtual objects, and/or virtual characters within the virtual space. The virtual entity may be controlled by a user's movement, as interpreted by sensors 902 communicating with the system. Display 950 may display a Patient View. The patient's real-world movements may be reflected by the avatar in the virtual environment. The virtual environment may be viewed in the HMD 201 in 3D, and may be monitored on the clinician tablet 210 in 2D. In particular embodiments, the VR environment is a game that may provide feedback and rewards based on the patient's ability to complete activities. Data related to the virtual avatar may be transmitted from the HMD 201 to the clinician tablet 210 to the cloud, where it may be stored for analysis.

The computing environment 900 may also comprise a display 970, which may be connected via transmitter 972. Display 970 may be a component of a clinician tablet 210. As an example and not by way of limitation, a supervisor or operator, such as a therapist, may securely log into the clinician tablet 210 coupled to the computing environment 900, to observe and direct the patient to participate in various activities, and may adjust the parameters of the activities to best suit the patient's ability level. Display 970 may depict at least one of a Spectator View, Live Avatar View, or Dual Perspective View.

Figure 10:
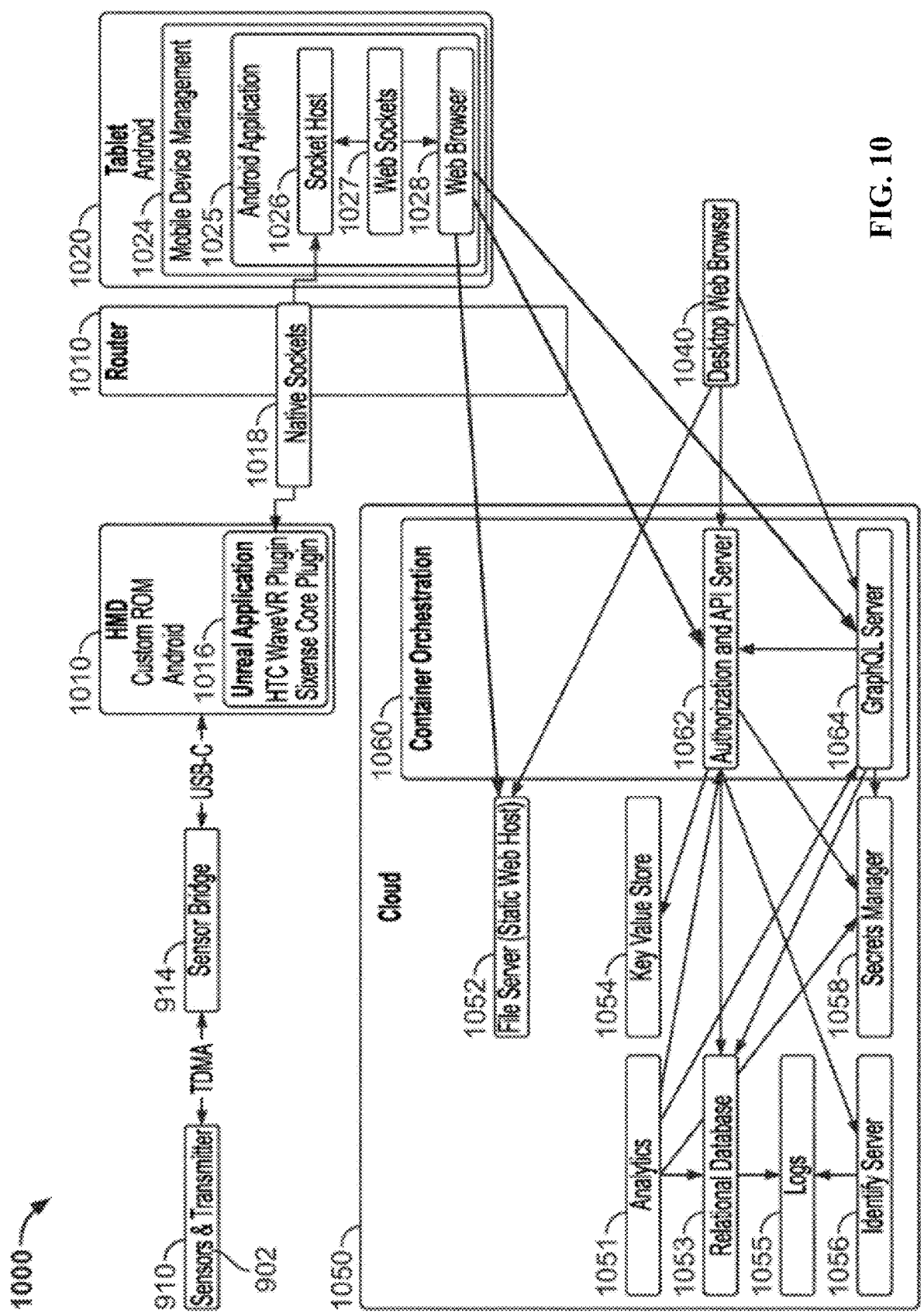
FIG. 10 is a diagram of an illustrative system, in accordance with particular embodiments of the disclosure.

FIG. 10 is a diagram of an illustrative VR system 1000, in accordance with particular embodiments of the disclosure. In particular embodiments, HMD 1010 may be the same as or similar to HMD 201 as disclosed herein. In particular embodiments, HMD 1010 may run a version of an Android operating system provided by a headset manufacturer (e.g., HTC), and the VR application may be an Unreal Application 1016 encoded in an Android package (.apk). The .apk comprises a set of custom plugins: WVR, WaveVR, SixenseCore, SixenseLib, and MVICore. The WVR and WaveVR plugins allow Unreal Application 1016 to communicate with the VR headset's functionality. The SixenseCore, SixenseLib, and MVICore plugins allow Unreal Application 1016 to communicate with the HMD Accessory and sensors that communicate with the HMD 201 via USB-C. The Unreal Application comprises code that records the Position & Orientation (P&O) data of the hardware sensors and translates that data into a patient avatar that mimics the patient's motion within the VR environment. An avatar may be used, for example, to infer and measure the patient's real-world range of motion. The Unreal Application 1016 of the HMD includes an avatar solver as described, for example, below.

An operator device, e.g., the clinician tablet 1020, which may be the same as or similar to clinician tablet 210 as disclosed here, may run a native application (e.g., Android application) that allows an operator such as a physical therapist (PT) to control the patient's experience. The cloud server may include a combination of software that manages authentication, data storage & retrieval, and hosts the user interface which runs on the clinician tablet 1020. The cloud server may be accessed by the clinician tablet 210.

The tablet software may include a mobile device management 1024 (MDM) layer, configured to control what software may operate on clinician tablet 1020, enable/disable software remotely, and remotely upgrade the native application.

The tablet software may include a native application, e.g., Android Application 1025, configured to allow an operator to control the HMD Software. The native application, in turn, comprises two parts: (1) a socket host 1026 configured to receive native socket communications from the HMD 1010 and translate that content into web sockets, e.g., web sockets 1027, that a web browser can easily interpret; and (2) a web browser 1028, which may be displayed on the tablet screen. The web browser may receive data from the HMD 1010 via the socket host 1026, which translates the HMD's native socket communication 1018 into web sockets 1027, and receives its UI/UX information from a file server 1052 in cloud 1050. Web browser 1028 may incorporate a real time 3D engine, such as Babylon.js, using a JavaScript library for displaying 3D graphics in web browser 1028 via HTML5. As an example and not by way of limitation, a real time 3D engine, such as Babylon.js, may render 3D graphics, e.g., in web browser 1028 on clinician tablet 1020, based on received skeletal data from an avatar solver in the Unreal Engine 1016 stored and executed on HMD 1010.

The cloud software, e.g., cloud 1050, may have multiple distinct, interconnected parts configured to communicate with the tablet software, including, for example, Authorization and API Server 1062, GraphQL Server 1064, and File Server (Static Web Host) 1052.

In particular embodiments, Authorization and API Server 1062 may be used as a gatekeeper. For example, when an operator attempts to log in to the VR system 1000, the clinician tablet 1020 may communicate with the Authorization and API Server 1062. Authorization and API Server 1062 may ensure that interactions (e.g., queries, updates, etc.) are authorized based on session variables such as the operator's role, the organization associated with the operator, and/or the current patient. This server, or a group of servers, may communicate with several parts of the system: (a) a key value store 1054, which is a clustered session cache that stores and allows quick retrieval of session variables; (b) a GraphQL server 1064, as discussed below, which is used to access the back-end database in order to populate the key value store, and also used for particular calls to the application programming interface (API); (c) an identity server 1056 for handling the user login process; and (d) a secrets manager 1058 for injecting service passwords (relational database, identity database, identity server, key value store) into the environment in lieu of hard coding.

When the clinician tablet 1020 requests data, it may communicate with the GraphQL Server 1064, which may in turn communicate with: (1) the authorization and API server 1062, (2) the secrets manager 1058, and (3) a relational database 1053 storing data for the system. Data stored by the relational database 1053 may include, as an example and not by way of limitation, profile data, session data, game data, and motion data.

In particular embodiments, profile data may include information used to identify the patient, such as a name or an alias. Session data may comprise information about the patient's previous sessions, as well as, for example, a "free text" field into which the therapist can input unrestricted text, and a log 1055 of the patient's previous activity. Logs 1055 are typically used for session data and may include, for example, a total activity time, e.g., how long the patient was actively engaged with individual activities, an activity summary, e.g., a list of activities the patient performed and how long the patient engaged with each activity, and settings and results for each activity. Game data may incorporate information about the patient's progression through the game content of the VR world. Motion data may include specific range-of-motion (ROM) data that may be saved based on the patient's movement over the course of each activity and session, which may enable therapists to compare the patient's session data to previous sessions' data.

In particular embodiments, file server 1052 serves the tablet software's website as a static web host.

As disclosed herein, sensors may be configured to be interchangeably placed on a patient's body, and an automatic assignment may be performed to associate each sensor to its corresponding location placement on the patient's body.

In VR system 1000, if each sensor is not associated with the proper body location for the session, sensor data may be incorrect. If the sensor data is incorrect, the animation may reflect an error, the VR activity control may not function correctly, and the therapist's patient data may be unsuitable for comparison between sessions. Accordingly, opportunities for error with respect to sensor association should be avoided or mitigated.

VR system 1000 may need to identify, for example, whether the movement measurements reflect movement of an elbow or a wrist. VR system 1000 may need to also identify, for example, whether a movement occurs on the patient's left side or right side. As such, sensor data collection should be made with precision and accuracy to the extent possible. Errors in sensor data collection, such as associating a sensor with the wrong body part, may be detrimental to the outcome, success, or progress of a patient's therapy.

Errors in sensor data collection or assignment may result in sensor data being recorded in an improper field. As an example and not by way of limitation, sensor data recorded for the incorrect side of the patient's body and results based on that erroneous data may sabotage the patient's progress records. Improper data records could also potentially cause misdiagnosis and/or improper resulting treatment. Based on incorrect data, a therapist might introduce activities or exercises that could cause the patient to experience pain, or otherwise harm the patient or be detrimental to the patient's therapy. Misidentifying sensors and/or improperly placing sensors may lead to improper patient care, as well as potential patient injury.

In particular approaches, VR systems 1000 may have particular sensors for each body part to ensure data is collected for the proper body part. As an example and not by way of limitation, each sensor might have a particular shape. Such an approach may invite human error in placing the sensors, which could lead to mistakes, inappropriate activities, and patient injury. In order to minimize the risk of mistake, a physical therapist may benefit from spending additional time installing each sensor on the appropriate body part, although spending additional time may incur higher costs and/or may negatively impact the patient, e.g., causing the patient to lose focus during therapy.

In particular approaches, each sensor may be given an identifying label, although such an approach may be confusing, may result in user error in placing the sensors, and may require additional time and attention. For example, a "left" label indicating that a sensor is assigned to a patient's left upper arm could be mistaken for being oriented relative to the therapist's left side rather than the patient, which could result in the "left" sensor being placed on the right side of the patient. As a result, the left and right arms of the patient's virtual avatar may not properly correspond to the patient's left and right arms, which may produce erroneous data which could lead to potentially injurious patient activities on a weaker or underdeveloped arm, which may be detrimental to the outcome, success, or progress of the patient's therapy.

In particular approaches, VR systems 1000 may have identical sensors, but each sensor may be preassigned to a body part. Such systems may use physical labels for the sensors to ensure they are placed in the correct position. Sensors that are not immediately recognizable for each body part may result in potential issues including placement delay, swapped hemispheres, replacement difficulty, and other types of human error. Consequently, there exists a need for interchangeable, swappable sensors.

As disclosed herein, interchangeable sensors provide a solution that may reduce placement errors and minimize setup time. In particular embodiments, interchangeability of sensors may further facilitate storage of the sensors not in use. For example, interchangeable sensors may be stored interchangeably in charging docks within a portable container, which may allow for faster packing and retrieval. In such a case, packing sensors will not require that specific sensors are packed in specific docks, and may further allow for quick replacement of sensors that are inoperative or have an uncharged/low battery.

Interchangeable sensors may also be interchangeably positioned on the body, which may allow for easier setup, faster storage, and greater mobility. As an example and not by way of limitation, the VR system 1000 may be portable, which may allow therapists to visit multiple patients in different rooms of a medical building or, potentially, at their homes. In particular embodiments, interchangeable sensors may be stored in a charging unit, e.g., a mobile dock. FIG. 1 depicts a portable storage container. A mobile charging unit may have docks for each interchangeable sensor. When the interchangeable sensors are removed from their docks, the interchangeable sensors may be placed on the body in any order.

In particular embodiments, sensors may be attached to the patient's body using elastic bands, such as bands 205 depicted in FIGS. 4-8. As illustrated in FIG. 6B, sensors 202 may be placed in bands 205 prior to placement on a patient.

In particular embodiments, sensors 202 may be placed onto bands 205 by sliding them into the elasticized loops. As an example and not by way of limitation, sensors may be placed above the patient's elbows, on the back of the patient's hands, and at the patient's lower back (sacrum). In particular cases, sensors may be placed on bands already attached to a patient, or may be placed in bands before they are attached to the patient, which may provide the patient with comfort and safety in securing the sensors.

If the sensors are interchangeable, then each sensor may need to be assigned to a specific body part of the patient. Particular approaches may require manual assignment, which may diminish the efficiencies gained from having interchangeable sensors. Consequently, there exists a need to automatically assign each interchangeable sensor to the proper body part on which it is placed.

Figure 13:
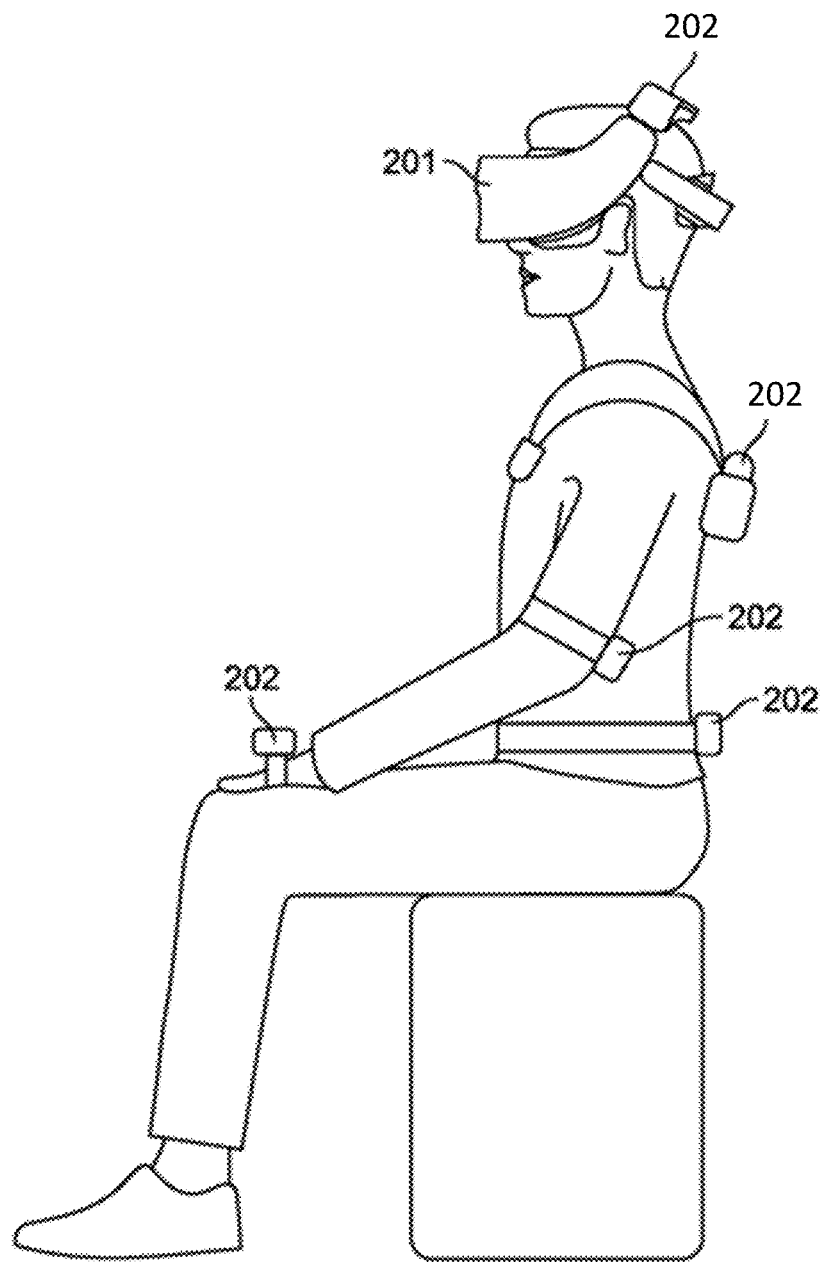
FIG. 13 is a diagram depicting a side view of a user interacting with an illustrative system, in accordance with particular embodiments of the disclosure.

As disclosed herein, interchangeable sensors can be automatically assigned to any body part during a calibration or syncing mode when the sensors are first placed on each patient. In particular embodiments, each of the interchangeable sensors are initially unassigned and, upon startup and placement, the interchangeable sensors may begin to auto-sync. Automatic Binding may allow for seamless, reduced-error setup, and may require minimal or no manual input. Once the interchangeable sensors are placed on the body, the system may automatically determine where on the body each sensor has been placed, and assign each sensor accordingly. Automatic binding may improve case of use by simplifying and expediting the setup and initiation process for operating the system. In particular embodiments, LEDs on the sensors may indicate whether the sensor is syncing or has been properly synced. An illustrative arrangement of sensors is shown in FIG. 13, which depicts a particular body position for setting up interchangeable sensors. Particular embodiments of sensor placement are also depicted in other figures, such as FIG. 2B.

In particular embodiments, upon startup and placement, sensors 202 will begin to auto-sync each of the wearable sensors 202 that are initially unassigned. Once the sensors 202 are placed on the body, the system may automatically determine where on the body each sensor 202 has been placed, and may assign each sensor its corresponding body part on the patient. In particular embodiments, sensors 202 placed on the body may provide position and orientation (P&O) data relative to a sensor with an emitter worn on a user's back. The P&O data may be analyzed by the host to determine the positioning of the various sensors. At least two variables may be used to determine the location of every sensor 202, such as, for example, height and hemisphere (e.g., right or left side). The sensor 202 with the highest position may be easily identified as the sensor on the HMD 201. Sensors 202 having a height closest to the emitter sensor may be assigned to the left and right elbows. Three sensors 202 may be detected at positions at approximately waist-height. The center-most of those three sensors 202 at waist-height may be assigned as the waist sensor, the left-most may be assigned as the left hand sensor, and the right-most may be assigned as the right hand sensor. In particular embodiments, knee and ankle sensors may be similarly identified by their hemisphere (left or right) and their height. Although an approach based on variable height and hemisphere is described in the example above, this should be understood as a general process to achieve auto-syncing. As an example and not by way of limitation, the magnetic field vectors received at each sensor may be processed before height and hemisphere can be determined. The magnetic field vectors may alternatively be processed to determine absolute distance from an emitter. In particular embodiments, if the patient moves his or her arms, accelerometers inside the sensors may help identify the hand/wrist and elbow sensors. During such arm movements, the patient's hands and wrists sensors may typically have the greatest acceleration of all the sensors 202, the elbow sensors may have an acceleration lower than the hands and wrists sensors, but greater acceleration than the other sensors 202. The rest of the sensors 202 may then be assigned determined based on height. The present disclosure may use other such processing methods, as known by those with skill in the art, or combinations of such methods, to determine relative sensor location. Auto-body-positioning may allow for seamless, error-proof setup, and requires no manual input. This auto-syncing feature may improve case of use by simplifying and expediting the process of setting up and starting the system, in order to quickly begin the physical therapy session.

Figure 11:
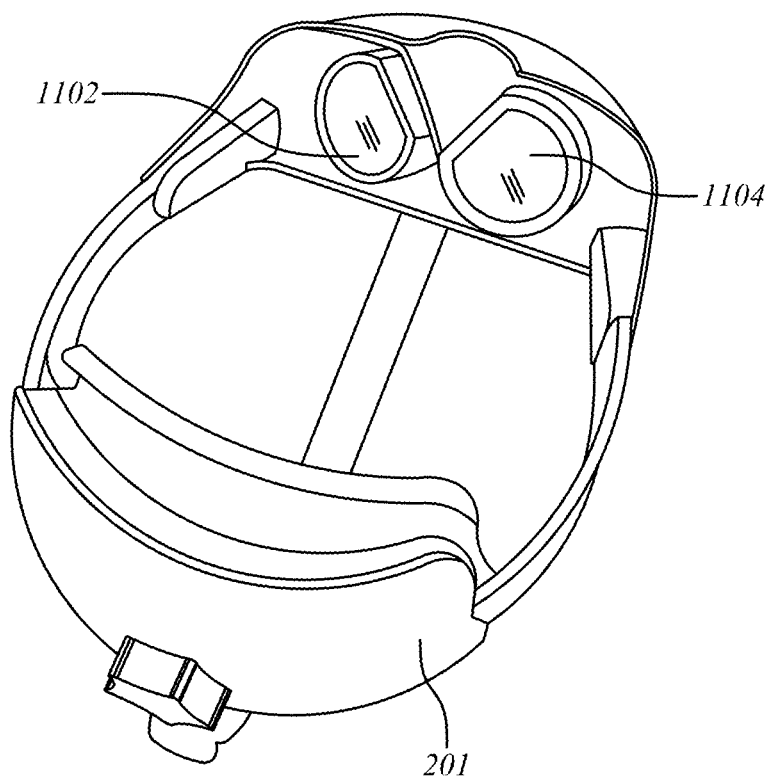
FIG. 11 is a diagram of a head-mounted display of an illustrative system, in accordance with particular embodiments of the disclosure.

FIG. 11 is an image of a head-mounted display of an illustrative system, in accordance with particular embodiments of the disclosure. For example, the head-mounted display 201 may comprise of one or multiple optical lenses. The one or multiple optical lenses may comprise a standard pair of lenses 1102 configured for users (e.g., patients or players) without any visual impairments (i.e., 20/20-vision without astigmatism) while using the head-mounted device. As an example, and not by way of limitation, the standard lenses 1102 may be Fresnel lenses. Additionally or alternatively, the multiple lenses of the head-mounted display may be adjustable (i.e., adjustable lens 1104). In particular embodiments, an adjustable lens 1104 may be removable from the head-mounted device when the user does not have any visual impairments that may affect the user's intended experience the VR environment. In particular embodiments, the head-mounted display may comprise more than one adjustable lens 1104 in front of each eye of the user. Different adjustable lenses 1104 may each be configured to address a particular visual impairment. For example, different optical lenses of the HMD may be configured to adjust a brightness and/or perspective to compensate for a particular visual impairment (e.g., farsightedness). In particular embodiments, a standard lens 1102 and an adjustable lens 1104 may be integrated as one integrated lens, which may be configured to change optical properties based on external stimuli (e.g., mechanical torque, electrical current, etc.). For example, the HMD 201 may apply an external force (e.g., a compression and/or twisting force) to edges (e.g., circumference) of the integrated lens in order to change the optical properties, such as an index of refraction, of the integrated lens. Also, the HMD 201 may apply a small electrical current to the integrated lens to change the optical properties of the lens (e.g., index of refraction, light dispersion properties, thermo-expansion characteristics, focal length adjustments, etc.). In particular embodiments, the integrated lens may have a default configuration for users that do not have visual impairment in which no external forces are applied to the integrated lens. In particular embodiments, the integrated lens may have one or more additional configurations for users who have visual impairments such that the HMD 201 may mechanically adjust the integrated lens by applying one or more external forces to the integrated lens. In particular embodiments, the lenses 1102 and 1104 may be electrically or wirelessly connected to the HMD 201, and the HMD 201 may be configured to automatically execute visual adjustments to the optical lenses.

Figure 12:
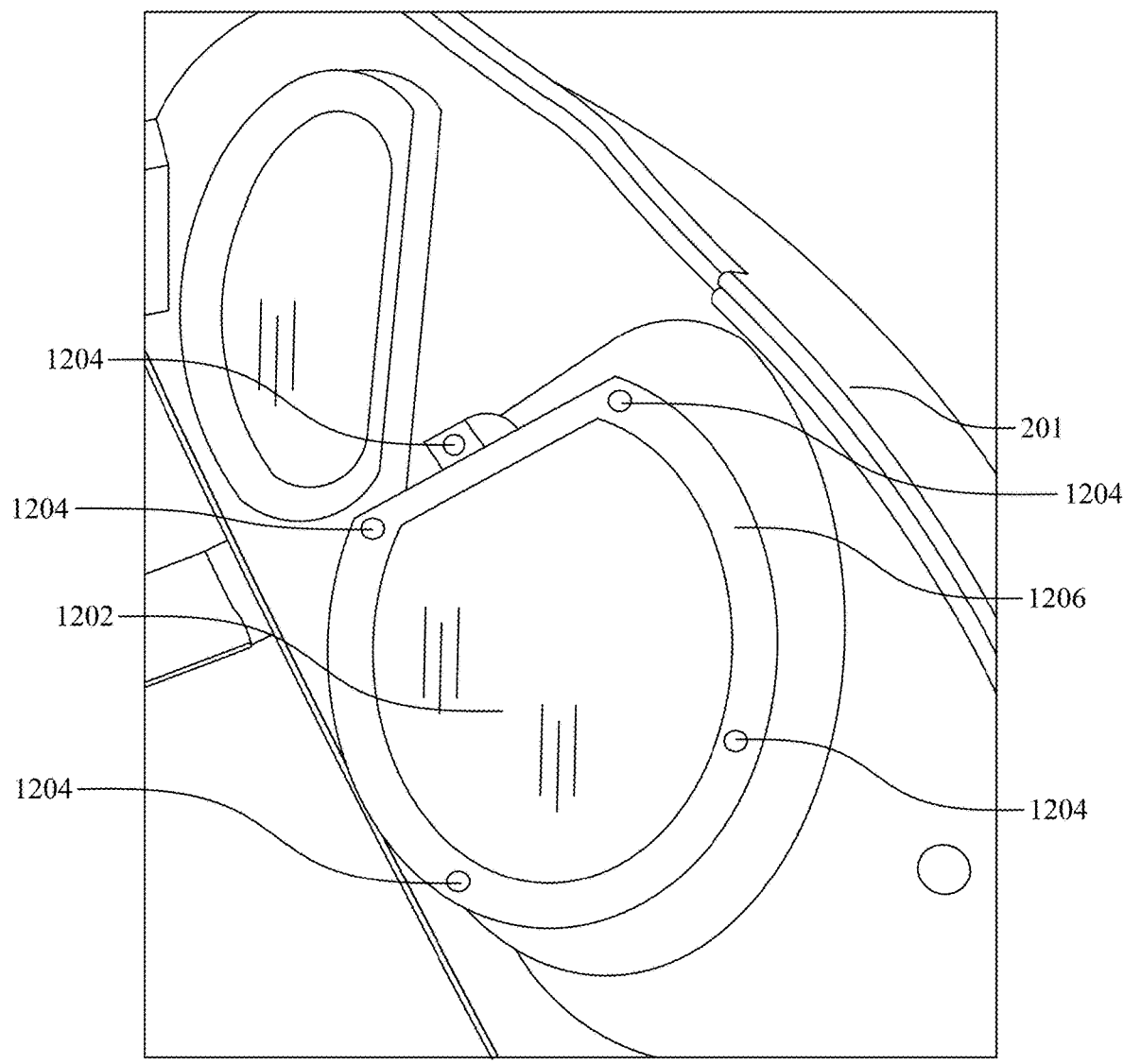
FIG. 12 is a diagram of a head-mounted display of an illustrative system, in accordance with particular embodiments of the disclosure.

FIG. 12 is an image of a head-mounted display of an illustrative system, in accordance with particular embodiments of the disclosure. In FIG. 12, for example, the HMD 201 may comprise an adjustable optical lens 1202 and a frame 1206 around the edge of the adjustable optical lens 1202. In particular embodiments, the frame 1206 may apply an external force (e.g., twisting, compression, tension) to the adjustable lens 1202 to adjust particular optical properties of the optical lens 1202. For example, the frame 1206 may apply a twist torque force, a compression force, or a tension force around the circumference of the optical lens 1202 to alter the index of refraction or other physical properties of the optical lens 1202. In particular embodiments, the frame 1206 may be electrically or wirelessly connected to the HMD 201. In particular embodiments, the HMD 201 may comprise more than one camera 1204, which may be configured to capture eye positions of the user, which may be used to determine eye movements and/or a focal point associated with the user. In particular embodiments, the HMD 201 may comprise multiple cameras 1204 to capture the eye positions of the user from multiple locations in the HMD. For example, the multiple cameras 1204 may be positioned in the middle of the HMD near a nose bridge of the user, in the corners of the optical lens 1202, around a radius of the optical lens 1202, and/or near an apex of the curve of the optical lens 1202. For example, the camera 1204 may detect one or more eye positions associated with a visual prompt displayed in the VR environment, and may send the eye positions to the processor 960 of the HMD 201, which may then identify cyc movements and/or focal points (e.g., for each eye) and may further identify one or more visual impairments associated with the user. The identified visual impairments may then be used to identify and implement one or more visual adjustments, for example, by adjusting one or more adjustable optical lenses 1202 and/or lens frames 1206.

FIG. 13 is a diagram depicting a side view of a user interacting with an illustrative system, in accordance with particular embodiments of the disclosure. In FIG. 13, for example, sensors 202 may be placed on the user's body to provide P&O data. For example, sensors 202 may be worn on a user's back (e.g., in a wireless transmitter module (WTM)). As described above, the P&O data may be analyzed by the host to determine the positioning of the various sensors. The position of each sensor may be identified by the example variables described above (e.g., height and hemisphere).

Figure 14:
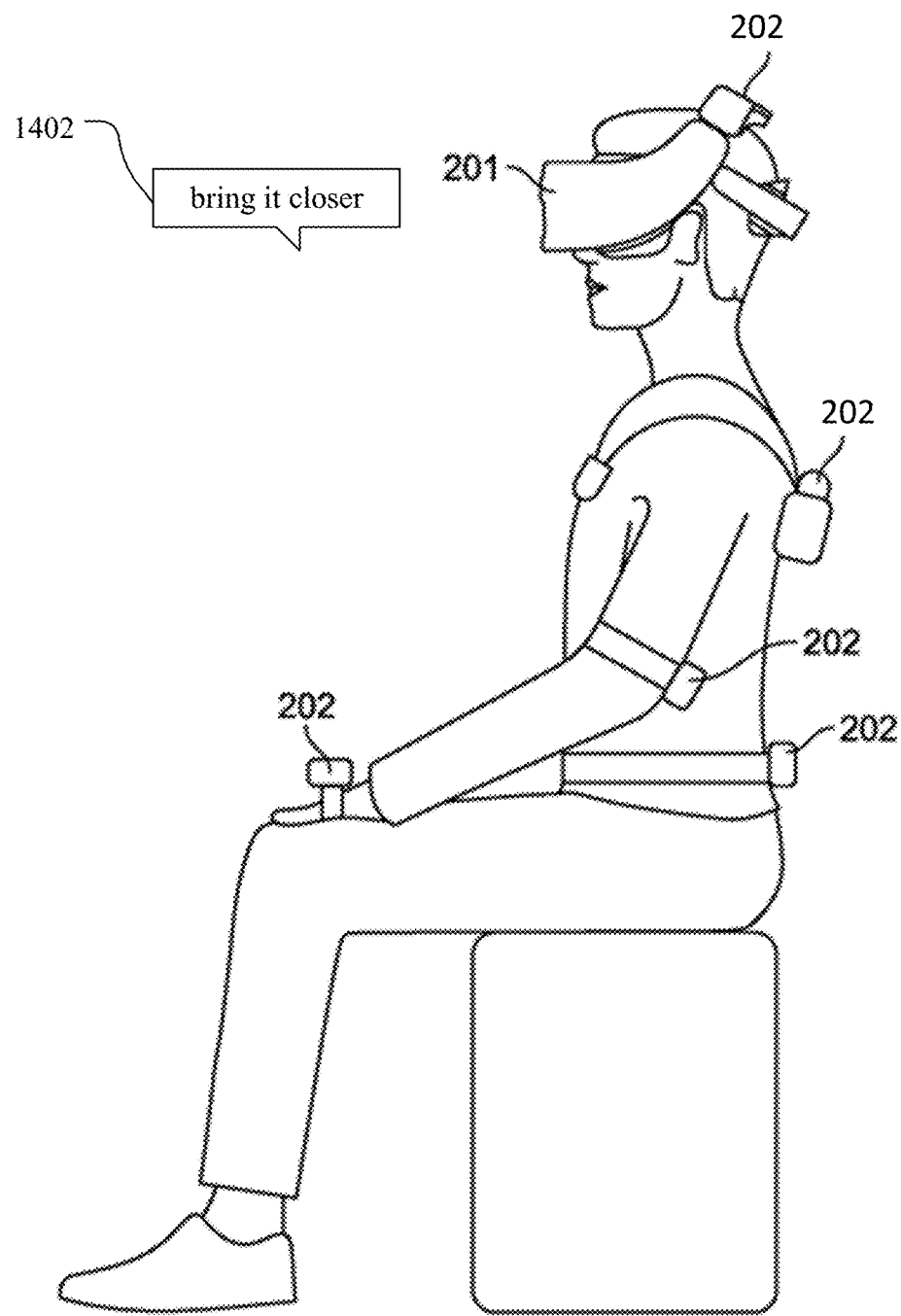
FIG. 14 is a diagram depicting a side view of an exemplary user position with a user audio response while using an illustrative system, in accordance with particular embodiments of the disclosure.

FIG. 14 is a diagram depicting a side view of a user providing an audio response while interacting with an illustrative system, in accordance with particular embodiments of the disclosure. The HMD may display visual content associated with, e.g., a game, a video, an image, or a visual prompt. The user may provide an audio command associated with a desired adjustment in the VR environment. For example, the visual content displayed may be configured to test a visual impairment of the user. In response, the user may provide an audio command 1402 to describe the visual impairment or a desired adjustment associated with the visual impairment to the HMD. For example, the HMD 201 may display an image with a target object (e.g., a balloon), and in response, the user may provide an audio command 1402 to "bring it closer" in order to change how the user perceives the rendered image, as will be described in further detail below. Additionally or alternatively, the HMD may automatically adjust the visual content for the user according to historical records associated with the user, which may be inadequate to compensate for the user's visual impairment under particular situations (e.g., blurred vision caused by various eye conditions, eye fatigue, etc.). The user may provide the audio command to for the HMD to adequately adjustment the visual content.

Figure 15:
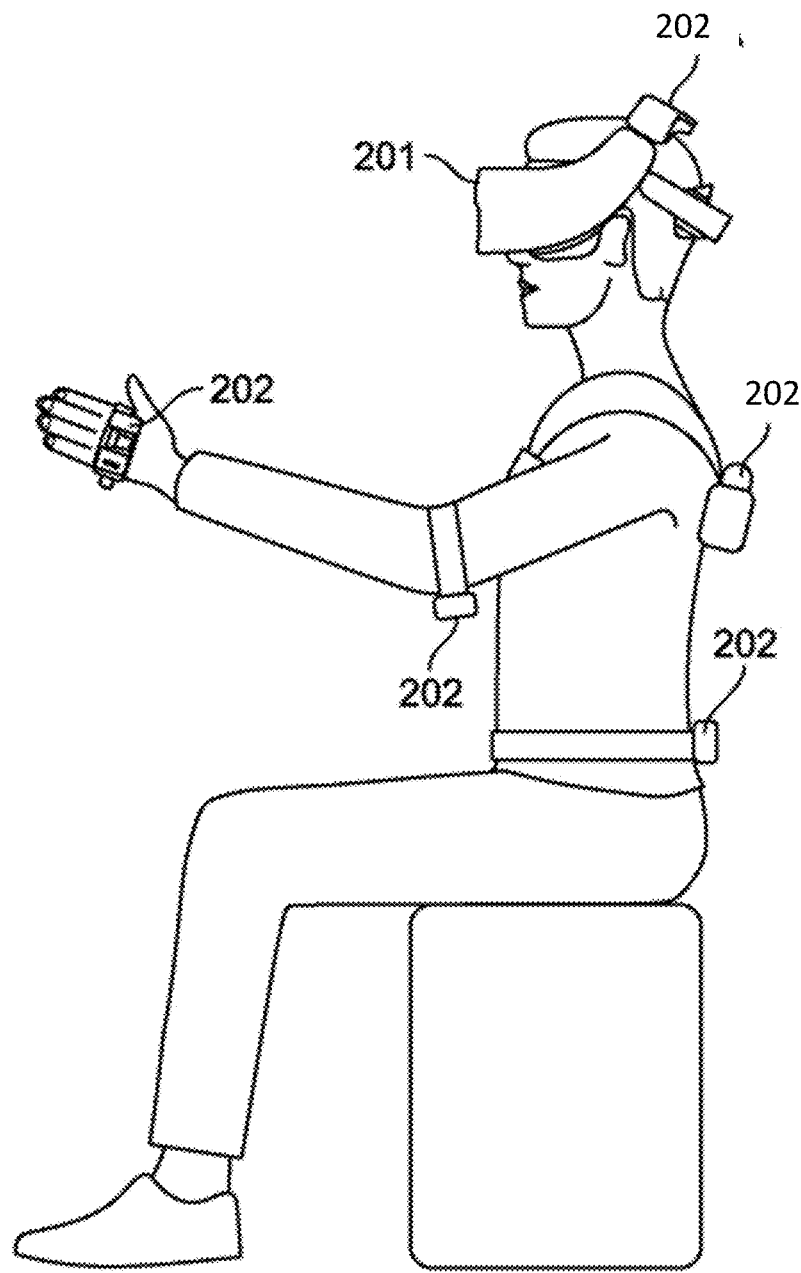
FIG. 15 is a diagram depicting a side view of an exemplary user position with a user gesture response while using an illustrative system, in accordance with particular embodiments of the disclosure.

FIG. 15 is a diagram depicting a side view of a user providing a gesture response while interacting with an illustrative system, in accordance with particular embodiments of the disclosure. As described above, sensors 202 may detect body movements of the user of the HMD 201. As depicted in FIG. 15, for example, the sensors 202 worn on the and arm and hand of the user may detect a hand gesture by the user. Hand gestures by the user may be associated with visual content displayed by the HMD 201. The user may use body movements such as hand gestures to provide input to the HMD 201 to indicate the user's visual impairment or a desired adjustment associated with the visual impairment based on the displayed visual content, as will be described in further detail below.

Figure 16:
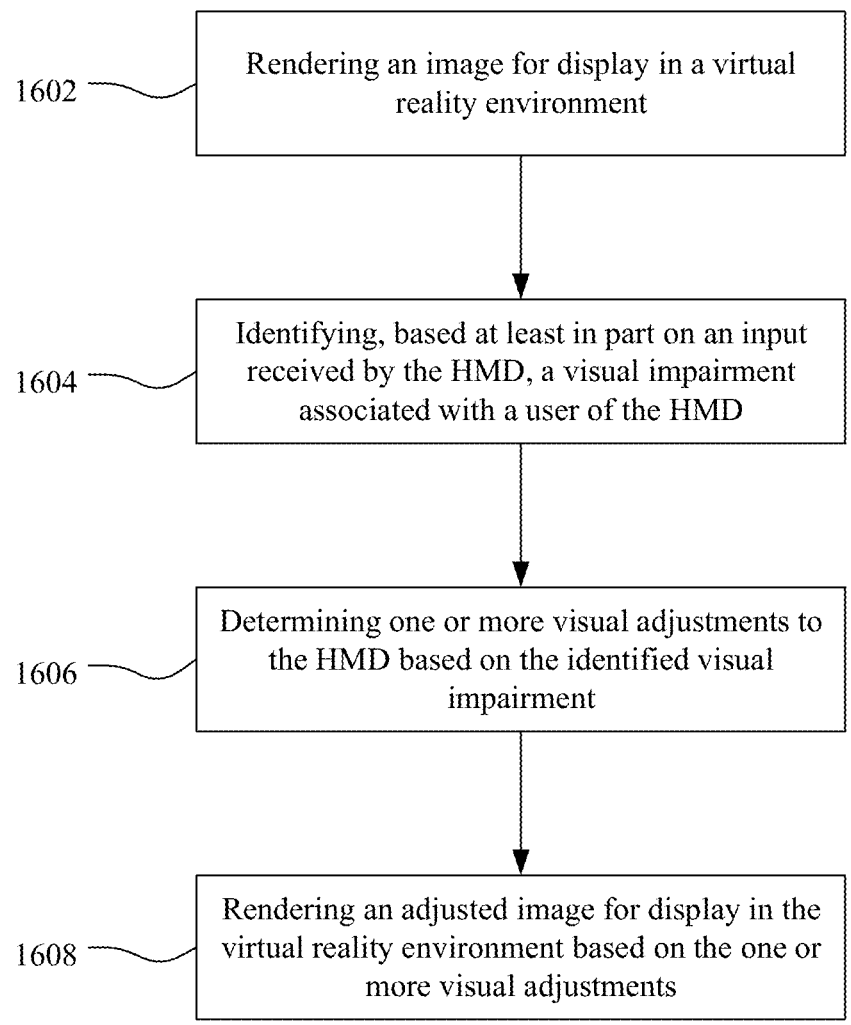
FIG. 16 depicts an illustrative flowchart of a process for compensating for visual impairments in a head mounted display, in accordance with particular embodiments of the disclosure.

FIG. 16 depicts an illustrative flowchart of a process for making visual adjustments in a VR environment displayed in a head-mounted display, in accordance with particular embodiments of the disclosure. At step 1602, the computer systems 900 associated with the HMD 201 may render an image for display in a VR environment (e.g., GPU rendering). The rendered image may be of standard image quality such that users with unimpaired vision (i.e., 20/20-vision without astigmatism) may see the rendered image clearly, which may enable the user to have an immersive experience in the rendered VR environment. At step 1604, the computer systems 900 may identify a visual impairment associated with a user of the HMD 201 based at least in part on an input received by the HMD 201. In particular embodiments, the input received by the HMD 201 may be provided by the user wearing the HMD 201. Additionally or alternatively, the input received by the HMD 201 may be provided by any individual associated with the user, such as a therapist or supervisor of the user. The therapist or supervisor of the user may monitor the user and the user experiences in the same room or remotely, and may provide inputs to the HMD based on the user's inputs in response to the rendered image, an observation of the user's behaviors by the therapist or supervisor, and/or information associated with the user and/or the HMD 201 that may be provided to the therapist or supervisor (e.g., through an interface such as the tablet 210). In particular embodiments, the user input may be in response to the image rendered at step 1602. At step 1606, the computer system 900 may determine one or more visual adjustments to the HMD 201 based on the identified visual impairment associated with the user. In particular embodiments, the visual adjustments may comprise adjustments to the rendered image displayed on the HMD 201. Additionally or alternatively, the visual adjustments may comprise adjustments to the optical lenses of the HMD 201. At step 1608, the computer systems 900 may render an adjusted image for display in the VR environment based on the one or more visual adjustments.

In particular embodiments, subsequent to or in response to the one or more visual adjustments, the computer systems 900 may detect one or more second user inputs, which may be used to determine additional visual adjustments. In particular embodiments, the HMD 201 may have one or more default settings configured for users with unimpaired vision (i.e., 20/20-vision without astigmatism), which may be applied by the HMD 201 on startup or at the start of a new session of interaction with the HMD 201 (e.g., treatment session, a game, a video). Different types of sessions may involve different types of visual content, which may each be partially or wholly reliant on certain aspects of unimpaired vision, and may therefore require different types of visual adjustments depending on the type of visual content and the type(s) of vision impairments associated with the user (e.g., nearsightedness, farsightedness, astigmatism). For example, visual adjustments for a greyscale image may comprise adjustments to an image brightness more than adjustments to an image perspective. In particular embodiments, visual adjustments for a given session may be reset for a subsequent session (e.g., power restart, new game session) in order to adaptively compensate for a user's visual impairment. For example, an adjusted rendered image in a first session may compensate for identified visual impairments of a first user, and the HMD 201 may be configured to adaptively compensate visual impairments for the first user during subsequent sessions. In particular embodiments, the HMD 201 may be configured to adaptively compensate visual impairments for one or more additional users during subsequent sessions.

In particular embodiments, the input received by the HMD 201 may comprise one or more user inputs received by the HMD 201 at step 1604. In particular embodiments, the user inputs may comprise one or more eye positions detected by the HMD 201. The HMD 201 may comprise a camera to detect eye positions and perform eye gaze tracking during a session of interaction with the HMD 201. The user inputs may be further based on a detection of one or more eye movements based on the one or more detected eye positions. The eye movements may comprise vestibular movement, saccades movement, smooth pursuit movements, and/or vergence movement. The user inputs may be further based on a detection of a focal point based on the one or more detected eye positions. For example, in the VR environment, the vergence movement of the eyes may be associated with an ability of the user's eyes to change the focus depth for objects rendered in a 3D world. In particular embodiments, the detected eye positions may be associated with and/or responsive to a visual prompt displayed in the VR environment. The eye movements and/or focal point may indicate the present visual conditions of the user. For example, but not by way of limitation, the HMD 201 may display a visual prompt comprising an English letters chart with letters displayed in different sizes (e.g., letter "E" chart), and the user input may correspond to eye positions detected when looking at a particular English letter on the chart. The particular English letter may be displayed such that a person with unimpaired vision (i.e., 20/20-vision without astigmatism) would see it clearly in a 3D world. The computer systems 900 may detect eye movements and/or a focal point based on the eye positions of the user when looking at the particular English letter, which may appear as blurry to the user. For example, the computer systems 900 may detect, based on the detected eye positions of the user, that the user's focal point when looking at the particular English letter is located at a particular position relative to the front of the user's retina. Continuing the example, the computer systems 900 may then identify that the user has visual impairment of nearsightedness based on the detected focal point. The computer systems 900 may then determine visual adjustments to compensate for the nearsightedness by altering a curvature of the optical lenses to increase the focal length of how the user perceives the rendered image in the VR environment. Additionally or alternatively, the computer systems 900 may adjust an image zoom for the rendered 3D image until the particular English letter can be clearly seen by the user. In another example, the HMD 201 may display a 3D object in the VR environment in order to detect the user's eye positions, eye movements, and/or focal point. For example, a 3D object displayed in the VR environment may be a house comprising visual details associated with the house (e.g., window, door, roof, chimney). The user may then be prompted to identify particular details of the house, which may cause the user to direct their eyes to the particular detail, in order to determine a visual impairment of the user.

In particular embodiments, the computer systems 900 may compare one or more of the detected eye positions to one or more reference eye positions associated with a rendered image. The reference eye positions may be predetermined and stored in association with the rendered image based on eye position data associated with users without visual impairments (i.e., 20/20-vision without astigmatism). The reference eye positions may be further associated with a reference focal length and/or a reference focal point. In particular embodiments, the computer systems 900 may then identify a visual impairment of the user based on the comparison of the detected eye positions and the reference eye positions. In particular embodiments, identifying the visual impairment of the user may be further based on a detection of one or more eye movements based on the one or more detected eye positions. In particular embodiments, identifying the visual impairment of the user may be further based on a detection of a focal point based on the one or more detected eye positions. In particular embodiments, identifying the visual impairment may be further based on a determination that the detected focal point is not correctly focused on retina (e.g., nearsightedness, farsightedness). In particular embodiments, the computer system 900 may further compare the detected focal point to a reference focal point, and may identify the visual impairment based on a comparison of the detected focal point and the reference focal point. In particular embodiments, identifying the visual impairment may be further based on a detection of multiple focal points (e.g., astigmatism). By way of example, as discussed, visual impairment may be detected using various ophthalmologic and/or optometry devices, sensors, or other diagnostic instruments to identify possible adjustments that may be needed. These devices may include wave-front lasers, ultra-sound devices, infrared devices, etc.

In particular embodiments, the input received by the HMD 201 may comprise one or more user inputs comprising one or more audio commands received by the HMD 201. The user may provide an audio command (e.g., audio command 1402) in response to a rendered image and/or in response to a visual prompt displayed in the VR environment. For example, in a VR environment configured for physical and/or cognitive rehabilitation treatment program, a patient wearing the HMD 201 may be prompted to track a moving 3D object. The HMD 201 may display an image frame in the VR environment configured for the treatment program, including the moving 3D object, and the user may respond by providing an audio response. For example, the user's audio response may be a description of the moving 3D object, a description of the user's perception of the moving 3D object such as "it's too blurry," or a description of a desired adjustment to the rendered image such as "bring it closer" or "make it bigger." The computer systems 900 may determine visual adjustments to the HMD 201 based on the received audio command. In particular embodiments, the user may provide the HMD 201 with an audio command through an audio interface. In particular embodiments, a natural language processor of the computer systems 900 associated with the HMD 201 may perform natural language processing of the received one or more audio commands. The audio command may be semantically parsed by the natural language processor for the computer systems 900 to determine the natural language content of the one or more audio commands, which may in turn be used to identify visual impairments and/or visual adjustments. In particular embodiments, the natural language processor of the computer systems 900 associated with the HMD 201 may semantically parse the one or more audio commands using a machine learning method (e.g., neural network) based on historical data collected by the HMD 201.

In particular embodiments, the input received by the HMD 201 may comprise one or more user inputs comprising one or more body movements received by the HMD 201. In particular embodiments, the HMD 201 may detect body movements through multiple sensors 202 placed on the user's body. The user may provide body movements in response to a rendered image or in response to a visual prompt displayed in the VR environment. The computer systems 900 may determine visual adjustments to the HMD 201 based on the user's body movements. For example, the user may use body gestures to respond to visual prompts that may include a 3D object or may use body gestures to make a selection in the VR environment in response to a displayed image. The computer systems 900 may render a series of image frames with differing image properties, such as, for example, image size, image brightness, and image contrast. The user may use hand gestures to select a displayed image that the user perceives as being compatible with their present visual conditions and/or adequately compensating for the user's visual impairments. In another example, the sensors 202 may detect body movements associated with the user's hands, arms, legs, back, waist, or head. The body movements may be associated with a tracking of a trajectory of a moving 3D object displayed in the VR environment. The computer systems 900 may compare a trajectory based on the body movement and the trajectory of a moving 3D object displayed in the VR environment to determine the visual impairments of the user.

In particular embodiments, the computer systems 900 associated with the HMD 201 may receive a plurality of inputs comprising eye positions, audio commands, and/or body movements, which may be received by a plurality of interfaces (e.g., eye gaze tracking interface, audio input interface, body movement sensors) of the HMD 201, each of which may be received at approximately the same time and/or may be received in association with the same rendered image. The computer systems 900 may synthesize each type of input received by the HMD 201, and may determine visual adjustments based on the synthesized input, which may be used to identify the user's visual impairments and/or determine visual adjustments.

In particular embodiments, the determined visual adjustments may comprise one or more adjustments to the image displayed in the VR environment. The one or more visual adjustments to the displayed image may comprise adjustments to one or more of image zoom, image perspective, image brightness, image sharpness, and image contrast. For example, and not by way of limitation, the visual adjustments to the image may comprise adjusting a measure of image zoom for the rendered image based on the identified visual impairment being nearsightedness. In another example, the visual adjustments to the image may comprise adjusting a measure of image sharpness when the rendered image includes numerous edge elements such that adjusting the image sharpness may enable a user with a visual impairment to perceive the image with an intended measure of image sharpness.

In particular embodiments, the visual adjustments to the image displayed in the VR environment may be based on identified visual impairments specific to the user's right eye or left eye. For example, the user's right eye and the user's left eye may have different visual impairments and/or require different measures of visual adjustments. In particular embodiments, the computer systems 900 may determine or identify a dominant eye of the user and may determine visual adjustments to the rendered image based primarily on the visual impairments of the user's dominant eye. In particular embodiments, the computer systems 900 may determine visual adjustments to the rendered images based on a binocular vision of the user.

In particular other embodiments, the determined visual adjustments may comprise one or more adjustments to one or more optical lenses of the HMD 201. In particular embodiments, the adjustments to the optical lenses of the HMD 201 may comprise altering a position of one or more of the optical lenses. For example, the adjustments to the optical lenses of the HMD 201 may comprise altering positions of one or more of the optical lenses along one or more axes relative to the HMD 201 and/or the user's eyes. For example, the positions of one or more of the optical lenses may be moved closer to the user's eyes or further away from the user's eyes. In another example, the positions of one or more of the optical lenses may be moved up, down, left, right, or in any angular or rotational direction (e.g., 30 degrees to the upper right).

In particular embodiments, the adjustments to the optical lenses of the HMD 201 may be adjustments to a focal length of the optical lenses. In particular embodiments, the adjustments to the optical lenses of the HMD 201 may comprise altering a shape of one or more of the optical lenses. Altering the shape of the optical lenses may comprise altering a curvature of the optical lenses to modify the focal length of the optical lenses. In particular embodiments, altering the curvature of the optical lenses may be performed by applying one or more external forces (e.g., compression, tension) to alter the curvature of one or more of the optical lenses. In particular embodiments, the HMD 201 may receive the user's inputs through the network 980 and may alter the optical properties (e.g., curvature of the optical lenses) automatically in response to receiving the users inputs. In particular embodiments, the adjustments to the optical lenses of the HMD 201 may comprise altering an index of refraction of one or more of the optical lenses. Altering an index of refraction may comprise applying a twist torque around the circumference of one or more of the optical lenses. Altering the index of refraction may further comprise determining a measure of twisting force to apply to the one or more optical lenses.

In particular embodiments, the computer systems 900 may determine one or more second visual adjustments based on the identified visual impairment and one or more second inputs received by the HMD 201. In particular embodiments, the one or more second inputs may be received in response to the adjusted image displayed in the VR environment, and the one or more second visual adjustments may correspond to a measure of compensation for a visual impairment in association with a second adjusted image. For example, and not by way of limitation, after rendering the adjusted image based on the visual adjustments, the computer systems 900 may determine the one or more second visual adjustments (e.g., a recalibration of the adjusted image) after a period of time (e.g., 5 minutes) and/or upon initiation of a new VR session (e.g., changing to a different VR application that may require different visual capabilities). In particular embodiments, the computer systems 900 may first apply adjustments to the optical lenses of the HMD 201 based on the identified visual impairment. The adjustments to the optical lenses may have limitations (e.g., capable of compensating for nearsightedness with moderate myopia no greater than −5.00 D) and may not adequately compensate for the user's visual impairment. Based at least in part on the limitations of the first adjustments, the computer systems 900 may determine one or more second adjustments to the rendered images to further compensate for the user's visual impairment. In particular embodiments, the one or more second adjustments may be determined based at least in part on one or more second inputs, which may be received in response to the first adjustments to the optical lenses of the HMD 201. In particular embodiments, the first visual adjustments may comprise one or more types of adjustments, which may comprise adjustments to the rendered images (e.g., image zoom, image perspective, image brightness, image sharpness, and an image contrast) and adjustments to the optical lenses (e.g., positions, shape, index of refraction), and the second visual adjustments may comprise one or more of the types of adjustments not included in the first visual adjustments.

Figure 17:
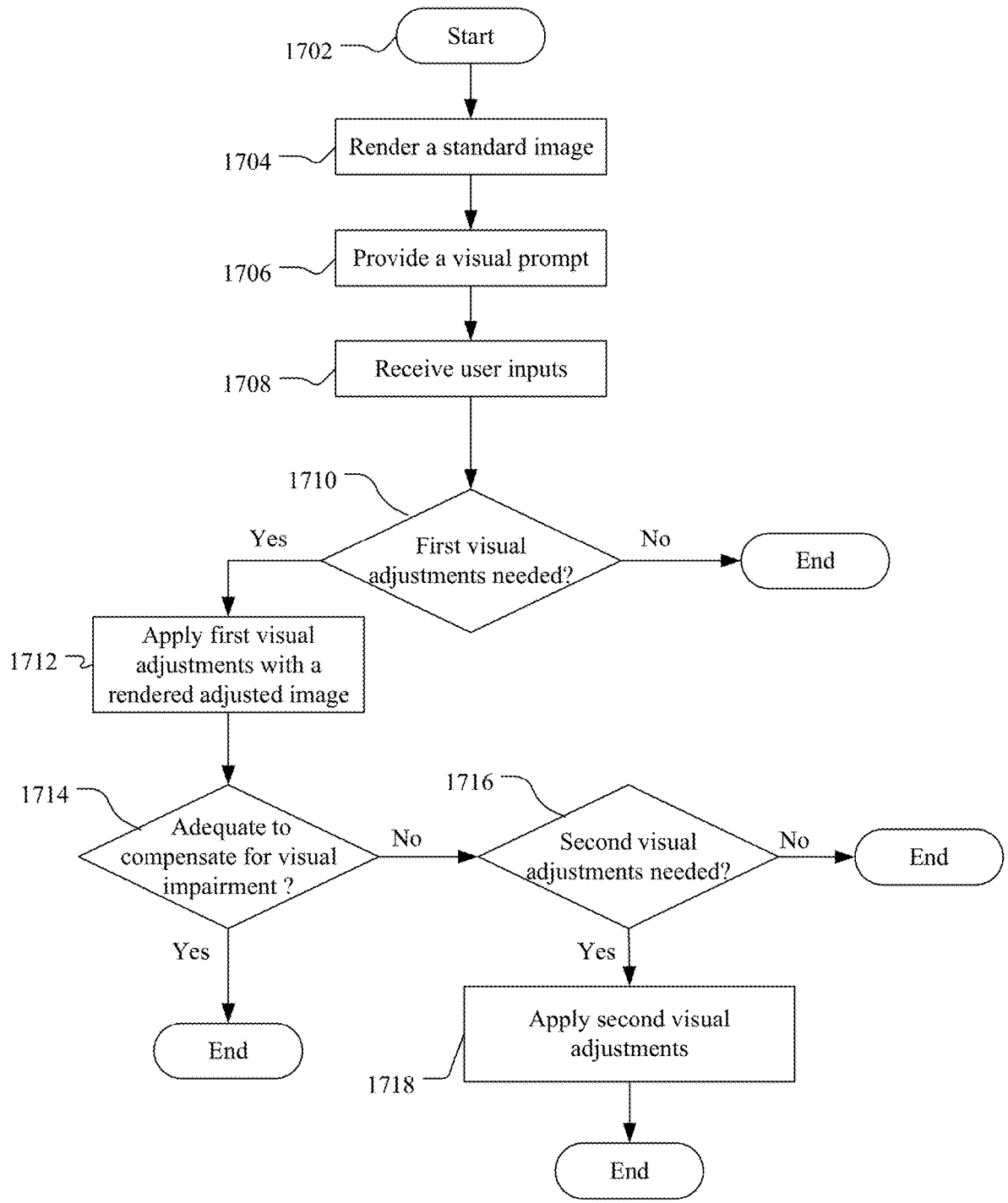
FIG. 17 depicts an illustrative flowchart of a process for determining at least one of a standard image adjustment and an optical lens adjustment, in accordance with particular embodiments of the disclosure.

FIG. 17 depicts an illustrative flowchart of a process for determining at least one of a standard image adjustment and an optical lenses adjustment, in accordance with particular embodiments of the disclosure. At step 1702, the HMD 201 may begin the process when the HMD 201 powers on, when a new VR session is initiated, or at the user's request. At step 1704, the computer systems 900 associated with the HMD 201 may render a standard image configured for a user without any visual impairments (i.e., 20/20-vision without astigmatism). The configuration for the standard image may be a default configuration or a customized configuration (e.g., a configuration customized by a user with a visual impairment). At step 1706, the HMD 201 may display a visual prompt associated with the standard image to test a visual condition of the user. At step 1708, the HMD 201 may receive one or more first user inputs associated with the visual prompt of the standard image. The user inputs may be based on one or more of the user's eye positions, audio commands, and body movements. At step 1710, the computer systems 900 associated with the HMD 201 may determine whether to apply a first visual adjustment based on the received one or more user inputs. At step 1712, the computer systems 900 associated with the HMD 201 may render an adjusted image based on the received user inputs. The HMD 201 may render the adjusted image based on the first visual adjustments, which may be associated with image properties (e.g., scale, perspective, brightness, sharpness, contrast). At step 1714, the method may determine whether the adjusted image adequately compensates for the user's identified visual impairment based on the received user inputs. Determining whether the adjusted image adequately compensates the identified visual impairment may be further based on one or more second user inputs, which may be received in response to the adjusted image. If the rendered adjusted image is determined to adequately compensate for the user's visual impairment, the HMD 201 may finish the adjusting process, and the HMD 201 may apply the first visual adjustments to additional image frames displayed to the user in the VR environment. If the rendered adjusted image is determined to not adequately compensate for the user's visual impairment, the computer systems 900 may be configured to further compensate for the user's visual impairment. In particular embodiments, the need for further compensation may be based on limitations of the first visual adjustments. For example, a limitation for the image zoom may be a maximum magnification, and for a user who may have moderate nearsightedness, the maximum magnification may still be inadequate to compensate for the user's visual impairment. If the rendered adjusted image is not adequate to compensate for the user's visual impairment, the user may further provide one or more second user inputs to the adjusted image. At step 1716, the computer systems 900 may determine whether to apply one or more second visual adjustments, which may be based at least in part on one or more second user inputs. At step 1718, the computer systems 900 may further compensate for the user's visual impairment based on the second visual adjustments. If the second visual adjustments are sufficient to compensate for the user's visual impairment, the HMD 201 may apply the first and second visual adjustments to additional image frames displayed to the user in the VR environment. In particular embodiments, at step 1718, the HMD 201 may additionally apply optical lens adjustments to cure the deficiency of the rendered adjusted image. The HMD 201 may finish the visual adjustment process once the user's visual impairment is adequately compensated with the first visual adjustment alone, and/or with a combination of the first visual adjustment and the second visual adjustments. In particular embodiments, the first visual adjustment and/or the second visual adjustments may be a plurality of types of adjustments, such as rendering adjusted images and/or applying optical lens adjustments. In particular embodiments, the rendered adjusted images may be based on adjustments to an image zoom, an image perspective, an image brightness, an image sharpness, and/or an image contrast. In particular embodiments, the optical lens adjustments may comprise adjustments to a position, a shape, a curvature, and/or an index of refraction of the one or more lenses of the HMD 201.

Figure 18:
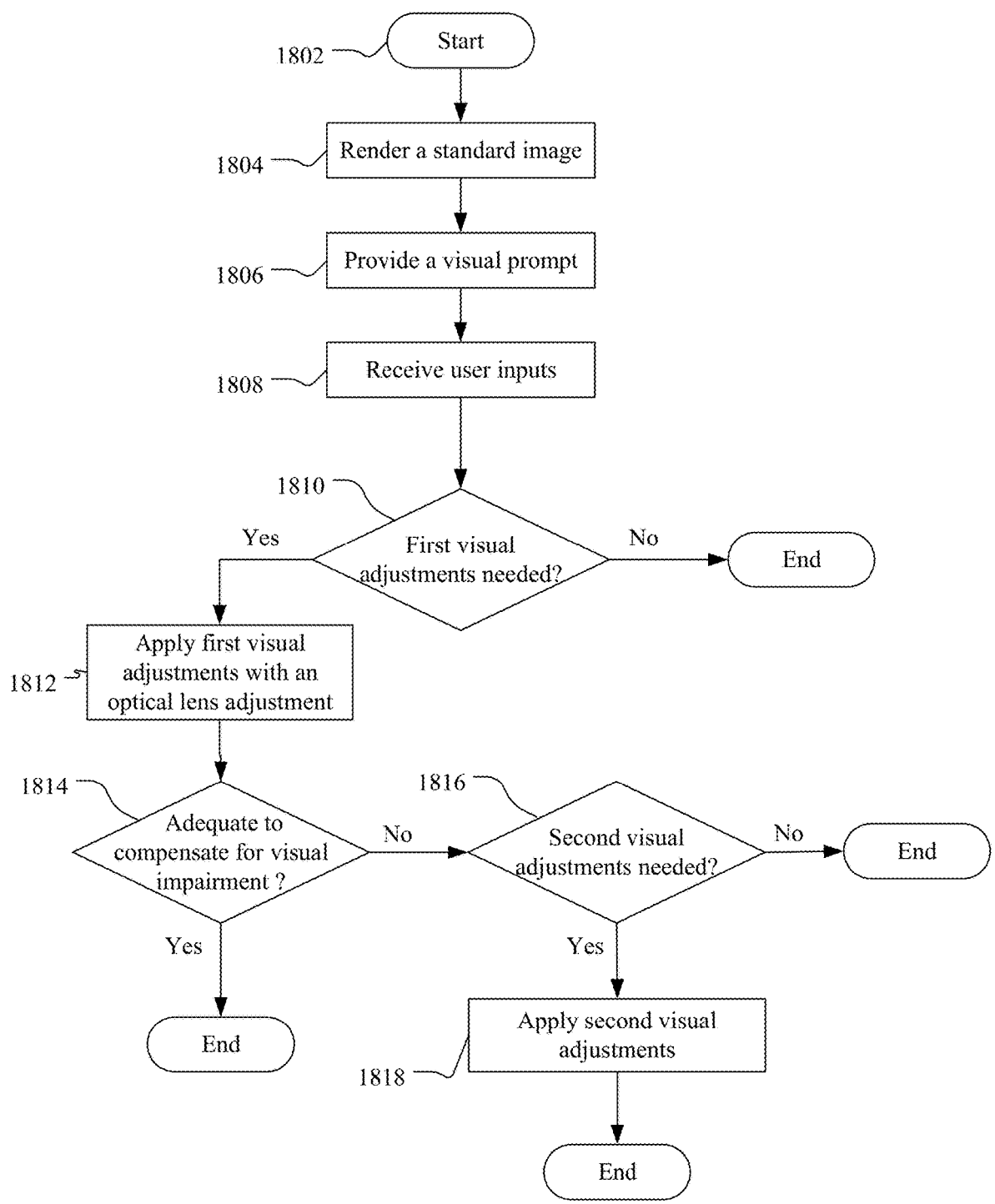
FIG. 18 depicts an illustrative flowchart of a process for determining at least one of a standard image adjustment and an optical lens adjustment, in accordance with particular embodiments of the disclosure.

FIG. 18 depicts an illustrative flowchart of a process for determining at least one of a standard image adjustment and an optical lenses adjustment, in accordance with particular embodiments of the disclosure. At step 1802, the HMD 201 may begin the process when the HMD 201 powers on, when a new VR session is initiated, or at the user's request. At step 1804, the computer systems 900 associated with the HMD 201 may render a standard image configured for a user without any visual impairments (i.e., 20/20-vision without astigmatism). The configuration for the standard image may be a default configuration or a customized configuration (e.g., a configuration customized by a user with a visual impairment). At step 1806, the HMD 201 may display a visual prompt associated with the standard image to test a visual condition of the user. At step 1808, the HMD 201 may receive one or more first user inputs associated with the visual prompt of the standard image. The user inputs may be based on one or more of the user's eye positions, audio commands, and body movements. At step 1810, the computer systems 900 associated with the HMD 201 may determine whether to apply a first visual adjustment based on the received one or more user inputs. At step 1812, the computer systems 900 associated with the HMD 201 may apply an optical lens adjustment for the first visual adjustment. The optical lens adjustment may comprise a position adjustment, a shape adjustment, and/or an index of refraction adjustment to one or more optical lenses of the HMD 201. At step 1814, the method may determine whether the optical lens adjustment adequately compensates for the user's identified visual impairment based on the received user inputs. Determining whether the optical lens adjustment adequately compensates the identified visual impairment may be further based on one or more second user inputs, which may be received in response to the optical lens adjustment applied by HMD 201. If the optical lens adjustment is determined to adequately compensate for the user's visual impairment, the HMD 201 may finish the adjusting process, and the HMD 201 may maintain the optical lens adjustment for the user's continued use of HMD 201. If the optical lens adjustment is determined to not adequately compensate for the user's visual impairment, the computer systems 900 may be configured to further compensate for the user's visual impairment. In particular embodiments, the need for further compensation may be based on limitations of the optical lenses. For example, a limitation of the optical lenses may be a maximum distance or angle the optical lenses may be adjusted to due to, for example, limited space around the optical lenses inside the HMD. For example, when applying a twisting force to an optical lens to alter the index of refraction, the angle of the optical lens may be limited to a maximum angle due to the limited space within the HMD. For example, the positions of the one or more optical lenses may be limited to a maximum distance due to the limited space within the HMD. Based on the limitations of the optical lenses, the identified visual impairment of the user may not be adequately compensated because, for example, the optical lens adjustment may not result in an adequate adjustment to a focal point/focal length. If the first visual adjustment applied with the optical lens adjustment is not adequate to compensate for the user's visual impairment, the user may further provide one or more second user inputs in response to the optical lens adjustment applied by HMD 201. At step 1816, the computer systems 900 may determine whether to apply one or more second visual adjustments, which may be based at least in part on one or more second user inputs. At step 1818, the computer systems 900 may further compensate for the user's visual impairment based on the second visual adjustments with one or more second optical lens adjustments. Additionally or alternatively, the HMD 201 may apply one or more second visual adjustments by rendering an adjusted image to cure the deficiency of the optical lens adjustment from the first visual adjustment. The HMD 201 may finish the visual adjustment process once the user's visual impairment is adequately compensated with the first visual adjustment alone, and/or with a combination of the first visual adjustment and the second visual adjustments. In particular embodiments, the first visual adjustment and/or the second visual adjustments may be a plurality of types of adjustments, such as rendering adjusted images, and/or applying optical lens adjustments. In particular embodiments, the rendered adjusted images may be based on adjustments to an image zoom, an image perspective, an image brightness, an image sharpness, and/or an image contrast. In particular embodiments, the optical lens adjustments may comprise adjustments to a position, a shape, a curvature, and/or an index of refraction of the one or more lenses of the HMD 201.

In particular embodiments, the HMD 201 may determine visual adjustments automatically when the user first starts using the HMD 201, when the user starts a new VR session, in response to receiving user inputs while the user is using the HMD 201, and/or at the request of the user or any individual associated with the user. In particular embodiments, the HMD may store information associated with visual impairments, visual adjustments, and/or configurations associated with a particular user. The HMD may be configured based on the stored information associated with the particular user. In particular embodiments, the HMD 201 may apply a first visual adjustment based on the stored information of a user profile, and may then apply one or more second visual adjustments based on user input received by HMD 201 after applying the first visual adjustment.

In particular embodiments, the HMD 201 may enable visual adjustments when the user is stationary. Continuous visual adjustment may cause discomfort and dizziness to the user if the user is in motion. As an example not by way of limitation, the HMD 201 may determine a stationary position of the user (e.g., sitting position, standing position), and may enable visual adjustments in response to determining the stationary position. Additionally or alternatively, the HMD may enable the first visual adjustments to partially compensate for the user's visual impairments automatically when the user is in motion, and perform the subsequent one or more second visual adjustments to adequately compensate for the user's visual impairments when the user is in a stationary position at a later time.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any of these embodiments may include any combination or permutation of any of the components, elements, features, functions, operations, or steps described or illustrated anywhere herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative. Additionally, although this disclosure describes or illustrates particular embodiments as providing particular advantages, particular embodiments may provide none, some, or all of these advantages.

What is claimed is:

1. A method comprising, by one or more computing systems associated with a head mounted display (HMD):
    rendering an initial image for display in a virtual reality environment;
    determining a first visual adjustment to the HMD based on an input received by the HMD, the input being associated with a visual impairment of a user of the HMD;
    determining that the first visual adjustment does not satisfy a threshold measure of compensation for the visual impairment of the user;
    determining a second visual adjustment to the HMD; and
    rendering an adjusted image for display in the virtual reality environment based on the first visual adjustment and the second visual adjustment.

2. The method of claim 1, wherein one or more of the first visual adjustment and the second visual adjustment comprises one or more adjustments to one or more image properties.

3. The method of claim 2, wherein the image properties comprise an image zoom, an image perspective, an image brightness, an image sharpness, and an image contrast.

4. The method of claim 1, wherein one or more of the first visual adjustment and the second visual adjustment comprise one or more adjustments to one or more optical lenses of the HMD.

5. The method of claim 4, wherein the adjustments to the optical lenses comprise altering a position of one or more of the optical lenses.

6. The method of claim 4, wherein the adjustments to the optical lenses comprise altering a shape of one or more of the optical lenses.

7. The method of claim 6, wherein altering the shape of one or more of the optical lenses comprises altering a curvature of one or more of the optical lenses.

8. The method of claim 4, wherein the adjustments to the optical lenses comprise altering an index of refraction of one or more of the optical lenses.

9. The method of claim 1, wherein the first visual adjustment is a different type of adjustment from the second visual adjustment.

10. The method of claim 1, wherein the initial image is rendered having an image quality associated with unimpaired vision.

11. The method of claim 1, further comprising:
rendering a visual prompt associated with the initial image for display in the virtual reality environment.

12. The method of claim 11, wherein the input received by the HMD is further associated with the visual prompt.

13. The method of claim 1, wherein the input received by the HMD comprises one or more user inputs received by the HMD.

14. The method of claim 13, wherein one or more of the user inputs comprise one or more eye positions of the user detected by the HMD.

15. The method of claim 13, wherein one or more of the user inputs comprise one or more audio commands detected by the HMD.

16. The method of claim 13, wherein one or more of the user inputs comprise one or more body movements detected by the HMD.

17. The method of claim 1, wherein the second visual adjustment to the HMD is determined based on a second input received by the HMD.

18. The method of claim 17, wherein the second input received by the HMD comprises one or more user inputs received by the HMD.

19. A computer system comprising: a plurality of sensors; one or more computing systems associated with a head mounted display (HMD); and one or more computer-readable non-transitory storage media embodying software that is operable when executed to:
render an initial image for display in a virtual reality environment;
determine a first visual adjustment to the HMD based on an input received by the HMD, the input being associated with a visual impairment of a user of the HMD;
determine that the first visual adjustment does not satisfy a threshold measure of compensation for the visual impairment of the user;
determine a second visual adjustment to the HMD; and
render an adjusted image for display in the virtual reality environment based on the first visual adjustment and the second visual adjustment.

20. One or more computer-readable non-transitory storage media embodying software that is operable when executed by one or more computing systems associated with a head mounted display (HMD) to:
render an initial image for display in a virtual reality environment;
determine a first visual adjustment to the HMD based on an input received by the HMD, the input being associated with a visual impairment of a user of the HMD;
determine that the first visual adjustment does not satisfy a threshold measure of compensation for the visual impairment of the user;
determine a second visual adjustment to the HMD; and
render an adjusted image for display in the virtual reality environment based on the first visual adjustment and the second visual adjustment.

* * * * *